(12) United States Patent
Fan et al.

(10) Patent No.: US 11,713,438 B2
(45) Date of Patent: Aug. 1, 2023

(54) SAMPLE CONTAINER FOR STABILIZING AND ALIGNING EXCISED BIOLOGICAL TISSUE SAMPLES FOR EX VIVO ANALYSIS

(71) Applicant: Perimeter Medical Imaging, Inc., Toronto (CA)

(72) Inventors: Chao Fan, Toronto (CA); Elizabeth A. Munro, Toronto (CA); David Rempel, Toronto (CA); James Jackson, Victoria (CA)

(73) Assignee: PERIMETER MEDICAL IMAGING, INC., Toronto (CA)

( * ) Notice: Subject to any disclaimer, the term of this patent is extended or adjusted under 35 U.S.C. 154(b) by 280 days.

(21) Appl. No.: 17/120,723

(22) Filed: Dec. 14, 2020

(65) Prior Publication Data

US 2021/0163864 A1   Jun. 3, 2021

Related U.S. Application Data

(60) Continuation of application No. 16/750,588, filed on Jan. 23, 2020, now Pat. No. 10,894,939, which is a
(Continued)

(51) Int. Cl.
*G01N 1/28* (2006.01)
*C12M 1/00* (2006.01)
(Continued)

(52) U.S. Cl.
CPC ......... *C12M 1/007* (2013.01); *A61B 10/0096* (2013.01); *B01L 3/505* (2013.01); *C12M 1/268* (2013.01); *C12M 23/14* (2013.01); *C12M 23/22* (2013.01); *G01N 1/28* (2013.01); *G01N 33/4833* (2013.01); *G01N 35/00029* (2013.01); *G02B 21/34* (2013.01); *G06T 7/0012* (2013.01); *B01L 2200/18* (2013.01); *B01L 2300/044* (2013.01);
(Continued)

(58) Field of Classification Search
None
See application file for complete search history.

(56) References Cited

U.S. PATENT DOCUMENTS

| 4,752,347 A | 6/1988 | Rada |
| 6,330,106 B1 | 12/2001 | Greenwald et al. |

(Continued)

OTHER PUBLICATIONS

European Search Report from corresponding European Application No. 18836143.0, dated Mar. 21, 2019, pp. 1-6, European Patent Office, Munich, Germany.

*Primary Examiner* — Jyoti Nagpaul
(74) *Attorney, Agent, or Firm* — Hauptman Ham, LLP

(57) ABSTRACT

Embodiments described herein relate to an apparatus for positioning and securing an excised biological tissue specimen for imaging and analysis. In some embodiments, an apparatus includes a sample bag defining an inner volume configured to receive a biological tissue sample, and a sealing member coupled to the sample bag. An imaging window is disposed and configured to be placed in contact with at least a portion of the biological tissue sample, and a positioning member is coupled to the imaging window and is configured to be disposed against the sealing member to substantially seal the inner volume. The positioning member includes a vacuum port disposed and configured to be aligned with a vacuum source to withdraw air from the inner volume of the sample bag.

54 Claims, 14 Drawing Sheets

Related U.S. Application Data division of application No. 16/171,980, filed on Oct. 26, 2018, now Pat. No. 10,577,573, which is a continuation of application No. PCT/CA2018/050874, filed on Jul. 18, 2018.

(60) Provisional application No. 62/533,728, filed on Jul. 18, 2017.

(51) Int. Cl.

| | | |
|---|---|---|
| *G01N 35/00* | (2006.01) | |
| *A61B 10/00* | (2006.01) | |
| *G02B 21/34* | (2006.01) | |
| *B01L 3/00* | (2006.01) | |
| *C12M 1/26* | (2006.01) | |
| *G01N 33/483* | (2006.01) | |
| *G06T 7/00* | (2017.01) | |
| *C12M 3/00* | (2006.01) | |

(52) U.S. Cl.
CPC ... *B01L 2300/047* (2013.01); *B01L 2300/048* (2013.01); *B01L 2300/049* (2013.01); *B01L 2300/123* (2013.01); *B01L 2400/049* (2013.01); *C12M 23/26* (2013.01); *C12M 23/46* (2013.01); *G01N 2035/00059* (2013.01)

(56) References Cited

U.S. PATENT DOCUMENTS

2015/0233798 A1   8/2015   Abeytunge et al.
2015/0277094 A1   10/2015   Eastman et al.

SAMPLE CONTAINER FOR STABILIZING AND ALIGNING EXCISED BIOLOGICAL TISSUE SAMPLES FOR EX VIVO ANALYSIS

CROSS-REFERENCE TO RELATED APPLICATIONS

This application is a continuation of U.S. patent application Ser. No. 16/750,588, filed Jan. 23, 2020, entitled "Sample Container For Stabilizing and Aligning Excised Biological Tissue Samples for Ex Vivo Analysis," which is a divisional of U.S. patent application Ser. No. 16/171,980, filed Oct. 26, 2018, now U.S. Pat. No. 10,577,573, entitled "Sample Container For Stabilizing and Aligning Excised Biological Tissue Samples for Ex Vivo Analysis," which is a continuation of International Patent Application No. PCT/CA2018/050874, filed Jul. 18, 2018, entitled "Sample Container for Stabilizing and Aligning Excised Biological Tissue Samples for Ex Vivo Analysis," which claims priority to, and the benefit of, U.S. Provisional Application No. 62/533,728 filed on Jul. 18, 2017, entitled "Sample Container for Stabilizing and Aligning Excised Biological Tissue Samples for Ex Vivo Analysis," the disclosures of which are hereby incorporated by reference in their entirety.

BACKGROUND

Embodiments described herein relate to an apparatus for positioning and securing an excised biological tissue specimen for imaging and analysis. In clinical and surgical situations, it is often helpful to image or otherwise analyze excised biological tissue to ensure a proper tumor margin was maintained around the mass of the biological tissue. Imaging and/or otherwise analyzing excised biological tissue samples can be difficult and time consuming, due in part to the fact that the excised tissue is often non-uniformly shaped and the sample needs to be maintained in the same position during analysis.

SUMMARY

Embodiments described herein relate to an apparatus for positioning and securing an excised biological tissue specimen for imaging and analysis. In some embodiments, an apparatus includes a sample bag defining an inner volume configured to receive a biological tissue sample, and a sealing member coupled to the sample bag. An imaging window is disposed and configured to be placed in contact with at least a portion of the biological tissue sample, and a positioning member is coupled to the imaging window and is configured to be disposed against the sealing member to substantially seal the inner volume. The positioning member includes a vacuum port disposed and configured to be aligned with a vacuum source to withdraw air from the inner volume of the sample bag.

DETAILED DESCRIPTION

Figure 1:
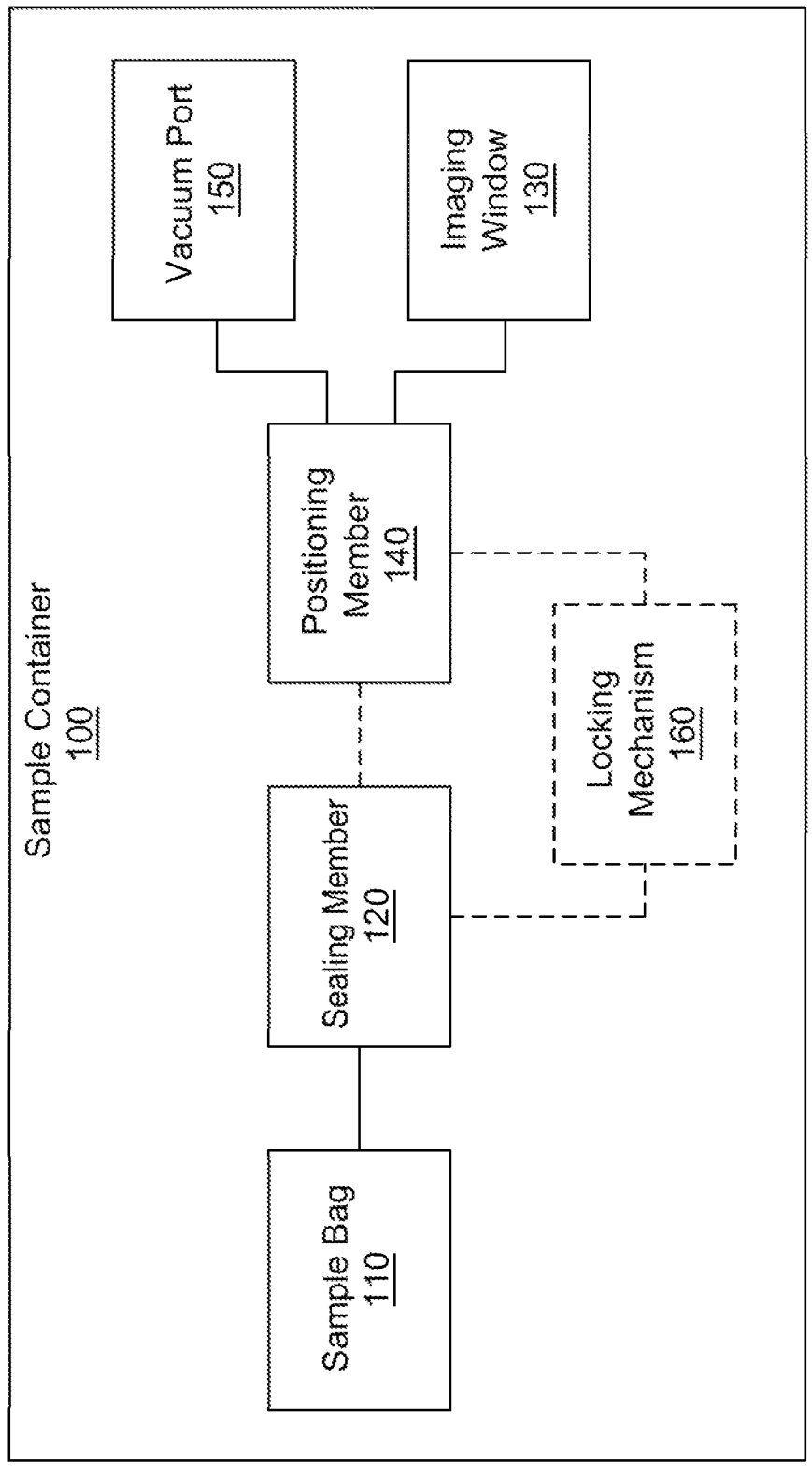
FIG. 1 is a schematic illustration of a sample container, according to an embodiment.

Embodiments described herein relate to an apparatus for positioning and securing an excised biological tissue specimen for imaging and/or analysis. In some embodiments, an apparatus includes a sample bag defining an inner volume configured to receive a biological tissue sample, and a sealing member coupled to the sample bag. An imaging window is disposed and configured to be placed in contact with at least a portion of the biological tissue sample, and a positioning member is coupled to the imaging window and is configured to be disposed against the sealing member to substantially seal the inner volume. The positioning member includes a vacuum port disposed and configured to be aligned with a vacuum source to withdraw air from the inner volume of the sample bag.

During certain surgical procedures, a biological sample is excised from a patient and then later analyzed to determine if the sample is diseased and/or if any abnormalities are present in the biological tissue (e.g., sarcoma, tumor, and/or carcinoma). The surgeon typically excises marginal tissue around the mass being removed to ensure that no cancerous or potentially cancerous cells are left in the patient, thereby reducing the likelihood of regrowth of the unwanted mass and/or the spread of cancer to other parts of the body following surgery. In some cases, the excised biological sample can be further examined using a wide array of analytical methodologies either within the surgical theater, outside the surgical theater, or by an off-site third party to ensure that sufficient marginal tissue was removed by the surgeon, e.g., after a lumpectomy. For example, optical coherence tomography (OCT) can be used to examine an excised mass of biological tissue as described in U.S. Patent Publication No. 2016/0040976 entitled, "System and Method for Wide Field OCT Imaging," filed Dec. 5, 2013 ("the '976 Publication"), the disclosure of which is incorporated herein by reference in its entirety. Other imaging and analysis methods can also be used for intrasurgical and/or extrasurgical analysis of biological samples.

In the clinical and surgical situations described above where an excised biological sample needs to be further examined or analyzed after excision, it is often desirable to properly contain and position the excised biological sample for further analysis. In other words, when imaging and/or analyzing a biological tissue sample, the sample needs to be placed in a fixed position or a substantially fixed position with respect to a lens, an aperture, a discharge point, or other reference point of the analysis or imaging device. For example, the practitioner may have to hold the biological sample in a very precise location for an extended period in order for the analysis or imaging device to successfully analyze and/or image the biological sample. Incorrectly positioned biological samples and/or movement of the biological samples during imaging/analysis can lead to lower quality images/results and can compromise the quality of patient care.

It should also be noted that the terms "coupled" or "coupling" as used herein can have several different meanings depending on the context in which these terms are used. For example, the terms coupled or coupling can have a mechanical, electrical or optical connotation. For example, depending on the context, the terms coupled or coupling may indicate that two elements or devices can be physically, electrically or optically connected to one another or connected to one another through one or more intermediate elements or devices via a physical, electrical or optical element such as, but not limited to a wire, fiber optic cable or waveguide, for example.

As used herein, the term "about" and "approximately" generally mean plus or minus 10% of the value stated, for example about 250 µm would include 225 µm to 275 µm, approximately 1,000 µm would include 900 µm to 1,100 µm.

In the following passages, different aspects of the embodiments are defined in more detail. Each aspect so defined may be combined with any other aspect or aspects unless clearly indicated to the contrary. In particular, any feature indicated as being preferred or advantageous may be combined with at least one other feature or features indicated as being preferred or advantageous.

Described herein are various example embodiments of systems, apparatuses, and methods that can be used to accurately and precisely position an excised biological tissue sample relative to an imaging device during imaging and/or during a storage period. The systems, apparatuses, and methods described herein have various applications such as, but not limited to medical applications, inter- or intra-surgical analysis, veterinary applications, laboratory applications, and ex vivo analysis of excised tumors, growths, nodules, melanoma, appendages, organs, and other excised biological materials. A typical tissue sample has a surface area of approximately 200 cm$^2$ and the surface of the tissue sample may be irregular, leading to complications during imaging or analysis of the excised biological tissues. Excised tissue samples can also be difficult to handle without introducing contaminants and/or causing damage to the tissue sample during handling of the sample and prior to imaging or analysis. In order to reduce the difficulty of sample handling, increase the ease and repeatability of positioning and maintaining the position of samples during imaging or analysis, and reduce the likelihood of introducing contaminants to the tissue sample, systems, apparatuses, and methods described herein can be used.

In some embodiments, an apparatus for holding a biological tissue sample in a fixed position or a substantially fixed position during imaging can include a sample bag defining an inner volume and configured to hold the biological tissue during imaging. In some embodiments, the sample bag can have an opening and define a cavity therewithin. In some embodiments, the sample bag can be configured to receive the biological tissue sample and have a first volume in a first configuration and a second volume less than the first volume in a second configuration.

In some embodiments, the apparatus can include a sealing member coupled to the sample bag and configured to maintain the sample bag in an airtight condition. In some embodiments, the sealing member can be coupled to a circumference of the opening of the sample bag.

In some embodiments, the apparatus can include an imaging window disposed and configured to be placed in contact with at least a portion of the biological tissue sample. In other words, the biological tissue sample can be positioned within the sample bag and can rest upon the imaging window during use of the apparatus. In some embodiments, the imaging window can fit within the opening of the sample bag and/or an aperture of the sealing member. In some embodiments, the imaging window can be disposed within the opening of the sample bag, and a positioning member coupled to the imaging window and configured to be disposed against the sealing member. In some embodiments, the imaging window can be configured to be in contact with a portion of the biological tissue sample.

In some embodiments, the apparatus can include a positioning member coupled to the imaging window and configured to be disposed against the sealing member. In some embodiments, the positioning member can include a vacuum port or a plurality of vacuum ports disposed and configured to be aligned with a vacuum source to withdraw air from the inner volume of the sample bag. In some embodiments, the inner volume of the sample bag can be substantially sealed when the positioning member is disposed against the sealing member. In some embodiments, the vacuum source is a vacuum pump. In some embodiments, the vacuum port can be sealed such that a partial vacuum can be maintained within the apparatus once the vacuum source is disconnected. In some embodiments, the positioning member can include a first portion and a second portion, the sealing member disposed between the first portion and the second portion such that the inner volume is substantially sealed. In some embodiments, withdrawing air from the cavity of the sample bag moves the sample bag from the first configuration to the second configuration.

In some embodiments, the apparatus can include a locking mechanism configured to maintain the sealing member in contact with the positioning member. In some embodiments, the locking mechanism can include a channel, e.g., a channel having a first end that is substantially open and a second end that is substantially closed. In some embodiments, the apparatus can include an alignment element connected to the positioning member, a first alignment marking indicating the first end of the channel, and a second alignment marking indicating the second end of the channel. In some embodiments, the alignment element is configured to move between the first alignment marking and the second alignment marking as the positioning member is rotationally connected to an imaging device, a base, and/or a receiving member. In some embodiments, alignment between the alignment element and the second alignment marking indicates proper alignment of the vacuum port with the vacuum system or the plurality of vacuum ports with the vacuum system. In some embodiments, the vacuum system can include a corresponding vacuum port or plurality of vacuum ports disposed within the imaging device, the base, and/or the receiving member. In some embodiments, the locking mechanism can include a ridge protruding from a surface of the locking mechanism, the ridge dimensioned and configured to be lockably disposed within a channel defined within the imaging device, the base, and/or the receiving member.

In some embodiments, at least one of the sample bag, the sealing member, the imaging window, and the positioning member is reusable. In some embodiments, at least one of the sample bag, the sealing member, the imaging window, and the positioning member can be sterilized in an autoclave before reuse.

In some embodiments, the apparatus can include an electronic sensor configured to close a circuit when the vacuum port is properly aligned with the vacuum system and an indicator light connected to the circuit and configured to illuminate when the circuit is closed. In some embodiments, the apparatus can also or alternatively include an audible alarm connected to the circuit and configured to produce a sound when the circuit is closed.

In some embodiments, the apparatus can include the receiving member, the receiving member including or defining a channel to which a portion of the positioning member is configured to be disposed. In some embodiments, the portion of the positioning member can include a ridge or other element configured to fit snugly within the channel. In some embodiments, the ridge or other element of the positioning member can be or substantially be the same shape as the inner cavity of the channel defined by one or more walls of the channel. In some embodiments, the apparatus can include a plurality of registration points disposed about the receiving member and configured to arrest movement of the positioning member once the portion of the positioning member is disposed within the channel. In some embodiments, the registration points can include a tab, a tag, a stub, a protuberance, a bump, a roughened portion, or any other suitable feature disposed on or defined by the positioning member, locking mechanism, and/or the receiving member, the base, or the imaging device. In some embodiments, the registration points can disallow rotational movement of the positioning member and/or the locking mechanism with respect to the receiving member, the base, or the imaging device. In some embodiments, the registration points can be visual aids such that a user can discontinue rotational movement of the positioning member and/or the locking mechanism with respect to the receiving member, the base, or the imaging device once the registration point is aligned with a corresponding alignment marking or other feature. In some embodiments, the receiving member can be configured to be coupled to the imaging device or can be a part of the imaging device such that the biological tissue sample is securely positioned against the sample window and readily available for analysis. In some embodiments, analysis can include the communication of electromagnetic energy from the imaging device, through the sample window, to the biological tissue sample.

The present disclosure also describes methods for making and using an apparatus configured to accurately position the excised biological sample relative to the imaging device and for maintaining accurate positioning for a period of time. In some embodiments a method for holding a biological tissue sample in a substantially fixed position during imaging can include receiving the biological tissue sample into the inner volume of the sample bag, the sample bag coupled to the sealing member. In some embodiments, the method can also include disposing the imaging window into contact with a portion of the biological tissue sample. In some embodiments, the imaging window can be disposed within or against a surface of the positioning member and/or the locking mechanism. In some embodiments, the method can include coupling the positioning member to the imaging window to form a sample container such that the biological tissue sample is substantially sealed within the sample container. In other words, after disposing the excised biological tissue sample into the sample bag, the sample bag can be disposed though an opening or orifice of the positioning member or locking mechanism with the imaging window disposed therebetween. In some embodiments, when the biological tissue sample is disposed within the sample bag and sealed therewithin using the imaging window held in place by the positioning member and/or the locking mechanism, the sample container is thereby formed. In some embodiments, the method can further include removably locking the sample container to a receiving member, the receiving member being configured to hold the sample container in place with regard to the imaging device. In some embodiments, the method can further include withdrawing air from the inner volume of the sample bag. In some embodiments, withdrawing air from the inner volume of the sample bag can cause the sample bag to move from the first configuration to the second configuration. In some embodiments, in the second configuration, the sample bag is drawn substantially tightly about the biological tissue sample and holds the biological tissue sample in place against the imaging window. In some embodiments, disposing the image window into contact with the portion of the biological tissue sample to form the sample container can include rotatably locking the imaging window to a sealing member.

In some embodiments, a method for making the sample holder configured to hold a biological tissue sample in a substantially fixed position during imaging can include coupling a sample bag to an imaging window. In some embodiments, when the imaging window is coupled to the sample bag, the inner volume of the sample bag can be substantially airtight. In some embodiments, the method can include coupling the sample bag to a locking mechanism by disposing the sample bag through an aperture of the locking mechanism such that the imaging window is disposed against a surface of the locking mechanism. In some embodiments, the locking mechanism can define a channel and can include a first plurality of vacuum ports. In some embodiments, the channel can include a first end that is open and a second end that is closed. In some embodiments, the method can further include rotatably coupling the locking mechanism to a receiving member. In some embodiments, the receiving member can include a ridge configured to be slidably disposed within the channel and a second plurality of vacuum ports. In some embodiments, the second plurality of vacuum ports can be configured to be substantially aligned with the first plurality of ports when the locking mechanism is rotatably coupled to the receiving member.

FIG. 1 shows a schematic illustration of a sample container 100 (also referred to herein as "specimen container" or "sample holder") that includes a sample bag 110 defining an inner volume configured to receive the biological tissue sample (not shown), and a sealing member 120 coupled to the sample bag 110. In some embodiments, an imaging window 130 is disposed and configured to be placed in contact with at least a portion of the biological sample. In some embodiments, a positioning member 140 is coupled to the imaging window 130 and is configured to be disposed against the sealing member 120 to substantially seal the inner volume of the sample bag 110. In some embodiments, the positioning member 140 can include at least one vacuum port 150 disposed and configured to be aligned with a vacuum source to withdraw air from the inner volume of the sample bag 110. In some embodiments, the sample container 100 further includes a locking mechanism 160 configured to selectively engaged with at least one of the positioning member 140 and/or the sealing member 120.

In some embodiments, the sample bag 110 is dimensioned and configured to hold or contain the biological tissue sample) during analysis and/or for a period of time after analysis has been conducted. In some embodiments, the sample bag 110 is dimensioned and configured to hold or contain the biological tissue sample for an extended period of time, during which time the sample is stored and/or transported for additional analysis and/or imaging. In some embodiments, the sample bag 110 is dimensioned and configured to be in a first configuration in which the inner volume of the sample bag 110 is at or is substantially at a maximum. In some embodiments, the biological tissue sample can be disposed within the sample bag 110 when the sample bag 110 is in the first configuration. In some embodiments, withdrawing air from the sample bag 110 can transition the sample bag 110 from the first configuration to a second configuration in which the inner volume of the sample bag 110 is lower than in the first configuration. In some embodiments, once a portion of air is withdrawn from the sample bag 110, the inner volume of the sample bag 110 can be substantially similar to the volume of the biological tissue sample. In some embodiments, the portion of air removed from the sample bag 110 can create a partial vacuum within the sample bag 110. In some embodiments, when the sample bag 110 is in the second configuration, the sample bag 110 can hold the biological tissue sample in place against the imaging window 130.

In some embodiments, the sample holder 100 and any subcomponents thereof can be sterilized such that a contacting surface (inner surface) of the sample container 100 is substantially free of biological contaminants, bacteriological contaminants, viral contaminants, chemical contaminants, or other contaminants. In some embodiments, "substantially free of contaminants" refers to any amount of contaminant present at or below the detectable limit using currently available analytical methods and according to current good manufacturing practice (cGMP). In some embodiments, the sample container 100 can be sterilized chemically, thermally, using a liquid solvent, via bombardment of electromagnetic energy, via irradiation from a radiological source, vi any other suitable methods, or any combination thereof. In some embodiments, the sample container 100 (or portions thereof) can be autoclaved prior to use.

In some embodiments, the sample bag 110 can be made from any suitably flexible, deformable, and/or elastic material disclosed herein. In some embodiments, the sample bag 110 can be substantially transparent in order to allow the practitioner to view the sample contained within. In some embodiments, the sample bag 110 can be highly flexible, allowing a vacuum system, a practitioner, any other cause, or any combination thereof to draw the bag more closely around the sample. In some embodiments, the sample bag 110 can include a polymer, a rubber, a vinyl, a ethyl compound, an imide, polyvinyl chloride, polypropylene, polyethylene, polystyrene, nylon, polyethylene terephthalate, polyimide, polycarbonate, acrylonitrile butadiene, polyetheretherketone, polyurethane, and any admixtures thereof.

In some embodiments, the sample bag 110 can be sufficiently robust (e.g., thick and/or durable) to withstand vacuum being drawn on the substantially sealed sample container 100 without being damaged and/or without compromising the airtight seal. In some embodiments, a thickness of the sample bag 110 can be between about 10 µm and about 5 mm, between about 15 µm and about 4.5 mm, between about 30 µm and about 4 mm, between about 75 µm and about 3 mm, between about 100 µm and about 3 mm, between about 150 µm and about 2.5 mm, between about 200 µm and about 2 mm, between about 300 µm and about 2 mm, between about 500 µm and about 1.5 mm, and between about 750 µm and about 1 mm, inclusive of all ranges and values therebetween. In some embodiments, the thickness of the sample bag 110 can be greater than about 10 µm, greater than about 50 µm, greater than about 100 µm, greater than about 150 µm, greater than about 200 µm, greater than about 250 µm, greater than about 300 µm, greater than about 350 µm, greater than about 500 µm, greater than about 750 µm, greater than about 1 mm, greater than about 2 mm, greater than about 3 mm, greater than about 4 mm, or greater than about 5 mm, inclusive of all ranges and values therebetween. In some embodiments, the thickness of the sample bag 110 can be less than about 5 mm, about 4.5 mm, about 4 mm, about 3.5 mm, about 3 mm, about 2.5 mm, about 2 mm, about 1.5 mm, about 1 mm about 750 µm, about 500 µm, about 250 µm, about 150 µm, about 100 µm, about 50 µm, or about 10 µm, inclusive of all values and ranges therebetween.

In some embodiments, the sample bag 110 can be coupled to the sealing member 120. In some embodiments, the sample bag 110 can be coupled to the sealing member 120 by interposing a portion of the sample bag 110 between two or more portions (e.g., layers) of the sealing member 120. For example, the two portions or more of the sealing member 120 can be coupled mechanically, with an adhesive, thermally bonded, or any combination thereof. In some embodiments, the sample bag 110 can be coupled to the sealing member with an adhesive. In some embodiments, the sample bag 110 can be coupled to the sealing member 120 through a thermal fusing process. In some embodiments, the sample bag 110 can be coupled to the sealing member 120 through a thermochemical melding of the two materials. In some embodiments, the sample bag 110 can be formed from the sealing member 120. In some embodiments, the sample bag 110 can be formed by extruding the sealing member 120 with no center hole and then forming the sample bag 110 from the sealing member 120 through thermal and/or physical deformation (e.g., stretching) of a portion of the sealing member 120. In some embodiments, deformation of a portion of the sealing member 120 (e.g., in the center) can define an aperture of the sealing member 120 and the opening of the sample bag 110. In some embodiments, the deformed portion of the sealing member 120 can be deformed to form the sample bag 110 therefrom. In some embodiments, the portion (e.g., center) of the sealing member 120 can be deformed to the extent that the material becomes sufficiently elastic and/or deformable and such that the formed sample bag 110 can transition from the first configuration to the second configuration when air is withdrawn from the sample bag 110.

In some embodiments, the sample bag 110 maintains a first configuration when no vacuum is drawn against the sample container 100. In some embodiments, the sample bag 110 can be substantially extended to its most voluminous state in the first configuration. In other words, the inner volume of the sample bag 110 is at or near a maximum volume in the first configuration. In some embodiments, once vacuum is drawn on the sample container 100 by withdrawing air from the sample bag 110, the sample bag 110 can transition from the first configuration to a second configuration. In some embodiments, the inner volume of the sample bag 110 in the second configuration is less than the inner volume of the sample bag 110 in the first configuration. In some embodiments, the inner volume of the sample bag 110 in the second configuration can be substantially similar to the volume of the biological tissue sample. Said another way, once vacuum is drawn on the sample container 100 substantially all of the air is removed from the inner volume of the sample bag 110 such that the biological tissue sample occupies nearly 100% of the inner volume. In some embodiments, the sample bag 110 can transition to a third configuration once the vacuum system is disconnected from the sample container 100 or the partial vacuum is otherwise relieved. In some embodiments, the sample bag 110 can transition to the third configuration while the vacuum system is still connected and the sample container 100 remains under partial vacuum. In some embodiments, the inner volume of the sample bag 110 in the third configuration can be less than the inner volume of the sample bag 110 in the first configuration but greater than the inner volume of the sample bag 110 in the second configuration. In some embodiments, the sample bag 110 can move from the second configuration back to substantially the first configuration once the sample container 100 is disconnected from the vacuum system or air is otherwise communicated back into the sample bag 110. In some embodiments, the sample bag 110 can remain substantially in the second configuration once the sample container 100 is disconnected from the vacuum system or air is otherwise communicated back into the sample bag 110. In some embodiments, the sample bag 110 can remain substantially in the second configuration because the vacuum port 150 can be sealed closed such that air is not allowed to be communicated back in to the sample bag 110. In some embodiments, sealing the vacuum port 150 can allow for the movement of the sample container 100 between different imaging devices and/or can allow the biological tissue sample to be stored in the sample container 100 without becoming contaminated.

The sealing member 120 can be a gasket, the gasket coupled to the sample bag 110 such that a seal is formed between the sample bag 110 and the sealing member 120. In some embodiments, the sealing member 120 can be disposed against a surface to form a seal. In some embodiments, the sealing member 120 can be disposed between two surfaces in order to substantially seal the sample container 100. In some embodiments, the sealing member 120 can define a center hole (not shown). In some embodiments, the sealing member 120 can be placed into abutment with a surface of the positioning member 140 during use of the sample container 100. In some embodiments, the abutment of the sealing member 120 against the surface of the positioning member 140 creates a seal or partial seal between the inner volume of the sample bag 110 and the outside environment. In some embodiments, the positioning member 140 is connected to the sealing member 120 to form a releasable seal between a surface of the sealing member 120 and the surface of the positioning member 140. In some embodiments, the positioning member 140 is interposed between the sealing member 120 and the imaging device or aperture defined therein. In some embodiments, the sealing member 120 is interposed between the positioning member 140 and the imaging device or aperture defined therein. In some embodiments, the sealing member 120 substantially covers a top portion or top side of the positioning member 140.

In some embodiments, the sealing member 120 can be made from any suitably material, including but not limited to plastics, rubbers, synthetic rubbers, neoprene, polyethylene, polyethylene terephthalate, polytetrafluoroethylene, nitrile, silicone, fiberglass, polychlorotrifluoroethylene, buna rubber, viton, fluoropolymer, teflon, polyesters, high-density polyethylene, low-density polyethylene, ultrahigh-density polyethyelen, polyvinyl chloride, polyvinylidene chloride, polypropylene, polystyrene, high impact polystyrene, polyamides, acrylonitrile butadiene styrene, polycarbonate, polyethyelen-acrylonitrile butadienet styrene, poly-carbonate-acrylonitrile butadiene styrene, polyurethanes, maleimide, bismaleimide, melamine formaldehyde, phenolics, plastarch, polyepoxide, polyetheretherketone, polyetherimide, polyimide, polylactic acid, polymethyl methacrylate, polytetrafluoroethylene, urea-formaldehyde, furan, polysulfone, nylon, and admixtures thereof. In some embodiments, the sealing member 120 can include a single layer of any of the disclosed materials. In some embodiments, the sealing member 120 can include a plurality of layers joined together. In some embodiments, the sealing member can include two to eight layers of material, inclusive of all values and ranges therebetween. In some embodiments, each of the plurality of layers can have substantially the same dimensions and can be formed from the same material or mixture of materials. In some embodiments, at least one of the plurality of layers has a different dimension than at least one other layer. In some embodiments, at least one of the plurality of layers is made from a different material or mixture of materials than at least one other layer.

In some embodiments, the sealing member 120 can have a dimensional thickness measured in the direction perpendicular to the surface configured to contact the positioning member 140. In some embodiments, the sealing member 120 can have a thickness sufficient to provide a substantially airtight seal when positive pressure is applied against the sealing member 120. In some embodiments, the sealing member 120 can have a thickness sufficient to provide a substantially airtight seal when a vacuum is drawn against the sealing member 120. In some embodiments, the sealing member 120 can have a thickness between about 10 µm and about 25 mm, between about 250 µm and about 15 mm, between about 500 µm and about 10 mm, between about 750 µm and about 9 mm, between about 850 µm and about 8 mm, between about 1 mm and about 7 mm, between about 1 mm and about 6 mm, between about 1.5 mm and about 5 mm, and between about 2 mm and about 4 mm, inclusive of all ranges and values therebetween. In some embodiments, the sealing member 120 can have a thickness greater than about 10 µm, greater than about 50 µm, greater than about 100 µm, greater than about 250 µm, greater than about 500 µm, greater than about 750 µm, greater than about 1 mm, greater than about 3 mm, greater than about 5 mm, greater than about 7 mm, greater than about 9 mm, or greater than about 11 mm, inclusive of all ranges and values therebetween.

The imaging window 130 at least partially defines the inner volume of the sample container 100 along with the sample bag 110, and is configured to be placed against an imaging device such that the imaging device can take images of the biological sample through the imaging window 130. In some embodiments, the imaging window 130 can be configured to be placed in contact with at least a portion of the biological tissue sample. In some embodiments, the imaging window 130 can be dimensioned and configured to be planar. In some embodiments, the imaging window 130 can be dimensioned and configured to be concave, providing a depression or other such concavity that at least partially holds the biological tissue sample in place during analysis and/or imaging. In some embodiments, the imaging window 130 can be fixedly coupled to the positioning member 140. In some embodiments, the imaging window 130 can be removably coupled to the positioning member 140. In some embodiments, the imaging window 130 can be disposed within an aperture (not shown) defined by the positioning member 140. In some embodiments, the imaging window 130 can be formed from the same material and/or at the same time as the positioning member 140. In other words, the imaging window 130 can be non-delineable element of the positioning member 140 (i.e., integrally formed with the positioning member 140).

In some embodiments, the imaging window 130 can have a thickness sufficient to withstand any vacuum pressure disclosed herein. In some embodiments, the imaging window 130 can be thin enough so as to allow light particles, electromagnetic energy, or other energy forms to pass through the imaging window 130. In some embodiments, the thickness of the imaging window 130 can be between about 10 μm and about 15 mm, between about 250 μm and about 13 mm, between about 500 μm and about 10 mm, between about 750 μm and about 9 mm, between about 850 μm and about 8 mm, between about 1 mm and about 7 mm, between about 1 mm and about 6 mm, between about 1.5 mm and about 5 mm, and between about 2 mm and about 4 mm, inclusive of all ranges and values therebetween. In some embodiments, the thickness of the imaging window 130 can be greater than about 10 μm, greater than about 50 μm, greater than about 100 μm, greater than about 250 μm, greater than about 500 μm, greater than about 750 μm, greater than about 1 mm, greater than about 3 mm, greater than about 5 mm, greater than about 7 mm, greater than about 9 mm, greater than about 11 mm, greater than about 13 mm, or greater than about 15 mm, inclusive of all ranges and values therebetween.

In some embodiments, the imaging window 130 can be made from any suitably rigid, suitably strong, and suitably transparent material. In some embodiments, the imaging window 130 can be made of glass, borosilicate glass (e.g., Schott BK7 or H-K9L from CDGM Glass Company Ltd.), amorphous polyolefins, cyclo olefin polymers, cellulose acetate, high-density polyethylene, low-density polyethylene, high-impact polystyrene, polyetheretherketone, polyesters, polyvinyl chloride, polyvinylidene chloride, polypropylene, polyamides, acrylonitrile butadiene styrene, polyurethanes, poly(methyl methacrylate), polycarbonate, polyethylene, polyethylene terephthalate, polylactic acid, polyvinyl butyral, pyrex, nitrocellulose, acrylates, any other material disclosed herein, and any other material suitably transparent and durable to enable imaging/analysis while also withstanding partial vacuum conditions, and combinations or admixtures thereof.

As described herein, the positioning member 140 can be coupled to and/or integrally formed with the imaging window 130. In some embodiments, the positioning member 140 can be non-uniformly shaped and the sealing member 120 can be dimensioned and configured such that the abutment of the sealing member 120 against the positioning member 140 can result in the sample container 100 being substantially sealed.

In some embodiments, the shape of the positioning member 140 can be in the form of a torus, hemisphere, disk, hoop, ring, halo, circle, planar circle, cuboid, ellipsoid, sphere, cylinder, hexagonal prism, pentagonal prism, rhombus, frustum, irregular polygon, any other suitable shape, or combinations thereof. In some embodiments, the positioning member 140 defines the aperture approximately in the center of the positioning member 140, and the imaging window 130 is disposed within the aperture defined by the positioning member 140. In some embodiments, the imaging window 130 is coupled to the positioning member 140 such that a substantially airtight seal is formed. In some embodiments, the positioning member 140, the imaging window 130, the sealing member 120, and the sample bag 110 collectively define the inner volume in which the biological sample is disposed.

In some embodiments, the positioning member 140 can be dimensioned and configured to abut a portion of an imaging device. In some embodiments, the positioning member 140 can be configured to position the sample of biological tissue in three-dimensional space relative to a lens or probe of the imaging device. In some embodiments, the positioning member 140 can be disposed at least partially within a recess of the imaging device. In some embodiments, the positioning member 140 can include an alignment feature to help ensure the sample container 100 is properly positioned with respect to the imaging device. For example, in some embodiments, the positioning member 140 can include alignment markings, fiducial marks, protuberances, keys, mechanical stops, recesses and/or the like that are designed to mate with the imaging device so that the sample container 100 is properly positioned with respect to the imaging device. Similarly, the imaging device can include alignment markings, fiducial marks, protuberances, keys, mechanical stops, recesses and/or the like that are designed to mate with the sample container 100. In other words, either the sample container 100, the imaging device, or both can include alignment features to help ensure the sample container 100 is properly positioned with respect to the imaging device.

In some embodiments, the positioning member 140 can have an outer surface and an inner surface. In some embodiments, the inner surface of the positioning member 140 can define a groove or a plurality of grooves. In some embodiments, the groove can be substantially filled with a plurality of indents. In some embodiments, the inner surface of the positioning member 140 can include threads. In some embodiments, the threads on the inner surface of the positioning member 140 can be dimensioned and configured to engage receiving threads within an aperture of the imaging device.

In some embodiments, the positioning member 140 can further include a plurality of tabs on the outer surface. In some embodiments, the plurality of tabs is between two and six tabs, inclusive of all ranges and values therebetween.

In some embodiments, the positioning member 140 can be made of any suitable material, including but not limited to polyesters, polyethylene terephthalate, polyethylene, high-density polyethylene, polyvinyl chloride, polyvinylidene chloride, low-density polyethylene, polypropylene, polycarbonate, polystyrene, high impact polystyrene, poyamides, acrylonitrile butadiene styrene, polyethylene-acrylonitrile butadiene styrene, polycarbonate-Acrylonitrile butadiene styrene, polyurethanes, maleimide, bismaleimide, melamine formaldehyde, plastarch, phenolics, phenol formaldehydes, polyepoxide, polyetheretherketone, polyetherimide, polyimide, polylactic acid, polymethyl methacrylate, polytetrafluoroethylene, urea-formaldehyde, furan, silicone, polysulfone, natural rubber, synthetic rubber, carbon fiber, nylon, cotton, wood, aluminum, bismuth, chromium, cobalt, copper, gallium, gold, indium, iron, lead, magnesium, mercury, nickel, rhodium, scandium, silver, titanium, tin, zinc, steel, stainless steel, brass, bronze, and admixtures thereof.

In some embodiments, the diameter of the positioning member 140 is between about 1 cm and about 35 cm. In some embodiments, the diameter of the positioning member 140 is greater than about 1 cm, greater than about 3 cm, greater than about 5 cm, greater than about 10 cm, greater than about 15 cm, greater than about 20 cm, greater than about 25 cm, greater than about 30 cm, inclusive of all values or ranges therebetween. In some embodiments, the diameter of the positioning member 140 is between about 1 cm and about 30 cm, between about 2 cm and about 30 cm, between about 3 cm and about 25 cm, between about 4 cm and about 20 cm, between about 5 cm and about 15 cm, between about 6 cm and about 14 cm, between about 7 cm and about 13 cm, between about 8 cm and about 12 cm, between about 9 cm and about 11 cm, inclusive of all values and ranges therebetween. In some embodiments, the diameter of the positioning member 140 is less than about 3 cm, less than about less than about 5 cm, less than about 7 cm, less than about 9 cm, less than about 11 cm, less than about 13 cm, less than about 15 cm, less than about 17 cm, less than about 19 cm, less than about 21 cm, less than about 23 cm, less than about 25 cm, less than about 29 cm, less than about 31 cm, less than about 33 cm, less than about 35 cm, inclusive of all values and ranges therebetween.

The vacuum port 150 is dimensioned and configured to be aligned with (i.e., placed in fluid communication) a vacuum source (not shown), such that the vacuum source can draw at least a partial vacuum on the sample container 100. Said another way, when the vacuum port 150 is aligned with the vacuum source, air can be drawn out of the sample bag 110 via the vacuum port. In some embodiments, the vacuum source can be a part of the imaging device. In some embodiments, the vacuum port 150 can be used to releasably couple the sample container 100 to the imaging device via the vacuum system as the vacuum system draws a partial vacuum on the sample container 100 such that the sample bag 110 is drawn around the biological tissue sample to hold it in place against the imaging window 130 during imaging/analysis.

In some embodiments, the vacuum port 150 can be disposed within the positioning member 140. In some embodiments, the vacuum port 150 can be a single vacuum port. In some embodiments, the vacuum port 150 can be a plurality of vacuum ports. In some embodiments, the plurality of vacuum ports 150 can be between two and ten, between two and eight, between two and six, between two and five, between two and four, between two and three, greater than two, greater than four, greater than six, greater than eight, or greater than 10, inclusive of all ranges and value therebetween.

In some embodiments, the amount of vacuum drawn, as absolute pressure in atmospheres (atm), on the substantially airtight sample container 100 can be from about 0.01 atm to about 0.97 atm, from about 0.1 atm to about 0.95 atm, from about 0.15 atm to about 0.9 atm, from about 0.2 atm to about 0.85 atm, from about 0.25 atm to about 0.8 atm, from about 0.3 atm to about 0.75 atm, from about 0.35 atm to about 0.7 atm, from about 0.4 atm to about 0.65 atm, from about 0.45 atm to about 0.6 atm, and from about 0.5 atm to about 0.8 atm, inclusive of all values and ranges therebetween. In some embodiments, the amount of vacuum drawn as absolute pressure on the substantially airtight sample container 100 can be less than about 0.97 atm, less than about 0.95 atm, less than about 0.9 atm, less than about 0.8 atm, less than about 0.7 atm, less than about 0.6 atm, less than about 0.5 atm, less than about 0.4 atm, less than about 0.3 atm, less than about 0.2 atm, and less than about 0.1 atm, inclusive of all values and ranges therebetween.

In some embodiments, the plurality of vacuum ports 150 disposed within or adjacent to the positioning member 140 are evenly disposed circumferentially about the positioning member 140. In some embodiments, the evenly disposed vacuum ports 150 can at least partially cause the sample bag 110 to be drawn about the biological tissue sample more evenly and to hold the biological tissue sample in a more substantially fixed position against the imaging window 130.

In some embodiments, the vacuum port 150 can further include a valve (not shown). In some embodiments, the valve can be actuated closed in order to maintain a state of partial vacuum within the sample container 100. In some embodiments, the state of partial vacuum within the sample container 100 can be maintained for a period of time. In some embodiments, the state of partial vacuum within the sample container 100 can be maintained for a period of time in order to fix the biological tissue sample against the imaging window 130 during storage, transport, and/or additional analysis of the biological tissue sample without the need for a vacuum system to continuously maintain the vacuum conditions within the sample container 100 over the same period of time.

In some embodiments, drawing vacuum on the sample container 100 results in the sample bag 110 being drawn tightly around the biological tissue sample, holding the biological tissue sample substantially immovably on the imaging window 130. In some embodiments, the biological tissue sample is held substantially immovably in a particular positon by both the positioning member 140 being releasably locked with respect to the imaging device (i.e., within an aperture) using the locking mechanism 160, and the air within the inner volume of the sample bag 110 being substantially evacuated from the inner volume.

In some embodiments, the locking mechanism 160 can be coupled to at least one of the positioning member 140 and/or the sealing member 120. In some embodiments, the locking mechanism 160 can be coupled to both the positioning member 140 and the sealing member 120. In some embodiments, the locking mechanism 160 can be coupled to both the positioning member 140 and the imaging device. In some embodiments, the locking mechanism 160 is configured to lock the positioning member 140 against the imaging device. In some embodiments, the locking mechanism 160 is configured to lock the positioning member 140 in an aperture of the imaging device. In some embodiments, the locking mechanism 160 is disposed between the two portions of the positioning member 140 such that the two portions of the positioning member 140 can be locked together. In some embodiments, the locking mechanism 160 is disposed between the two portions of the positioning member 140, such that the sealing member 120 can be interposed between the two portions of the positioning member. In some embodiments, the locking mechanism 160 can be configured such that the positioning member 140 can be immovably connected to at least a portion of the sealing member 120.

In some embodiments, the locking mechanism 160 can be a first threaded element dimensioned and configured to rotationally engage with a second threaded element. In some embodiments, the first and/or second threaded element can include stops or extents. In some embodiments, the stops or extents can be a physical barrier at a precise point which halts further rotational and vertical motion of the positioning member 140.

In some embodiments, the locking mechanism 160 can be a feature of the sample container 100 that is separate and distinct from the positioning member 140. In some embodiments, the locking mechanism 160 can be a locking pin or bolt. In some embodiments, the locking mechanism 160 can be a strap. In some embodiments, the locking mechanism 160 can be a latch. In some embodiments, the locking mechanism 160 can be spring-loaded detents that are disposed within a depression once the positioning member 140 is appropriately positioned on a surface of the imaging device or within the aperture in a surface of the imaging device. In some embodiments, the locking mechanism 160 can include any combination of the features and elements included herein.

In some embodiments, the locking mechanism 160 can be made from polyvinyl chloride, polypropylene, polyethylene, polystyrene, nylon, polyethylene terephthalate, polyimide, polycarbonate, acrylonitrile butadiene, polyetheretherketone, polyurethane, steel, stainless steel, aluminum, copper, lead, zinc, silver, titanium, tin chromium, platinum, molybdenum, magnesium, cobalt, tungsten, manganese, mercury, cadmium, niobium, circonium, vanadium, tantalum, palladium, rhodium, beryllium, indium, thorium, iridium, lithium, lanthanum, barium, rhenium, carbon fiber, and any combinations or admixtures thereof.

Figure 2:
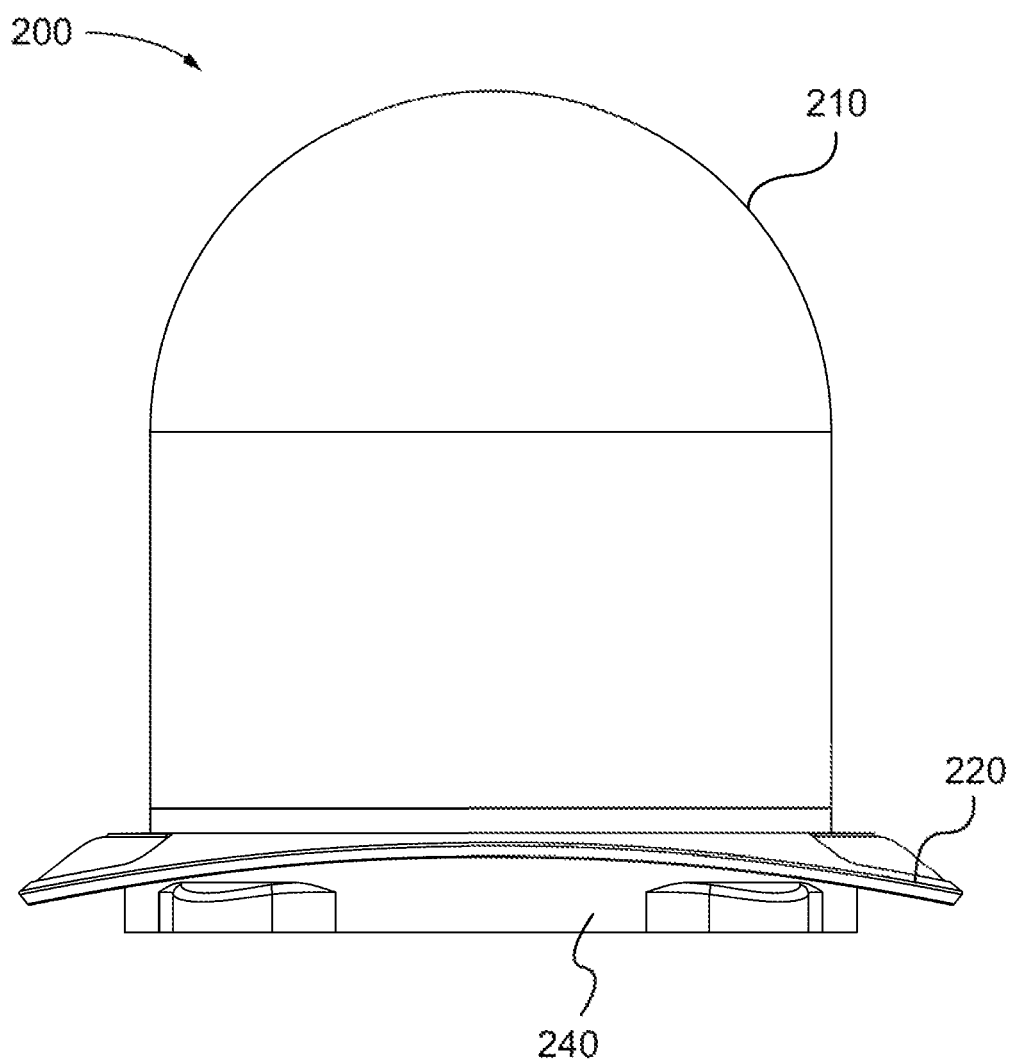
FIG. 2 is a side-view of the sample container, according to an embodiment.
Figure 3:
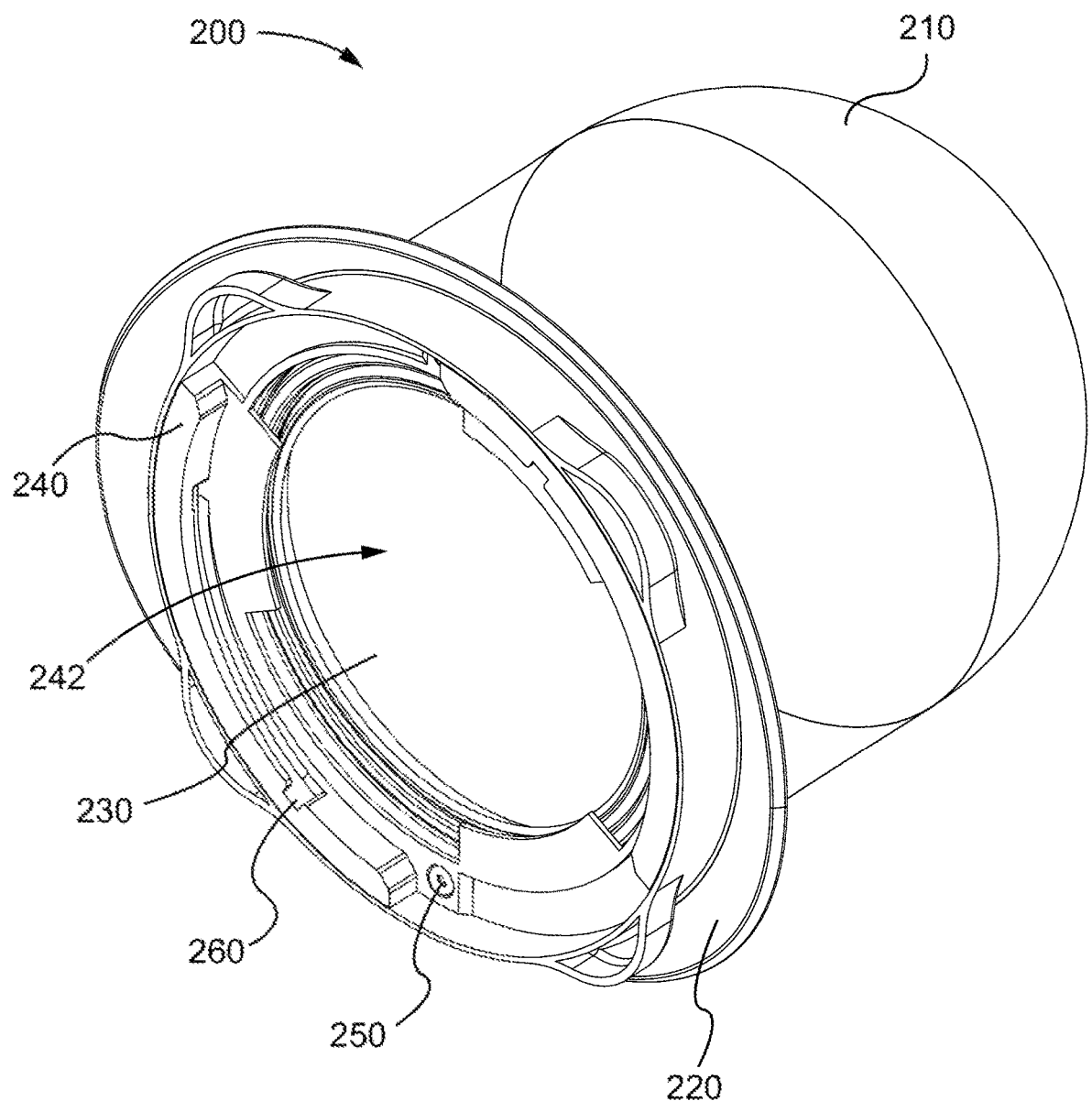
FIG. 3 is a perspective view of the sample container, according to an embodiment.
Figure 4:
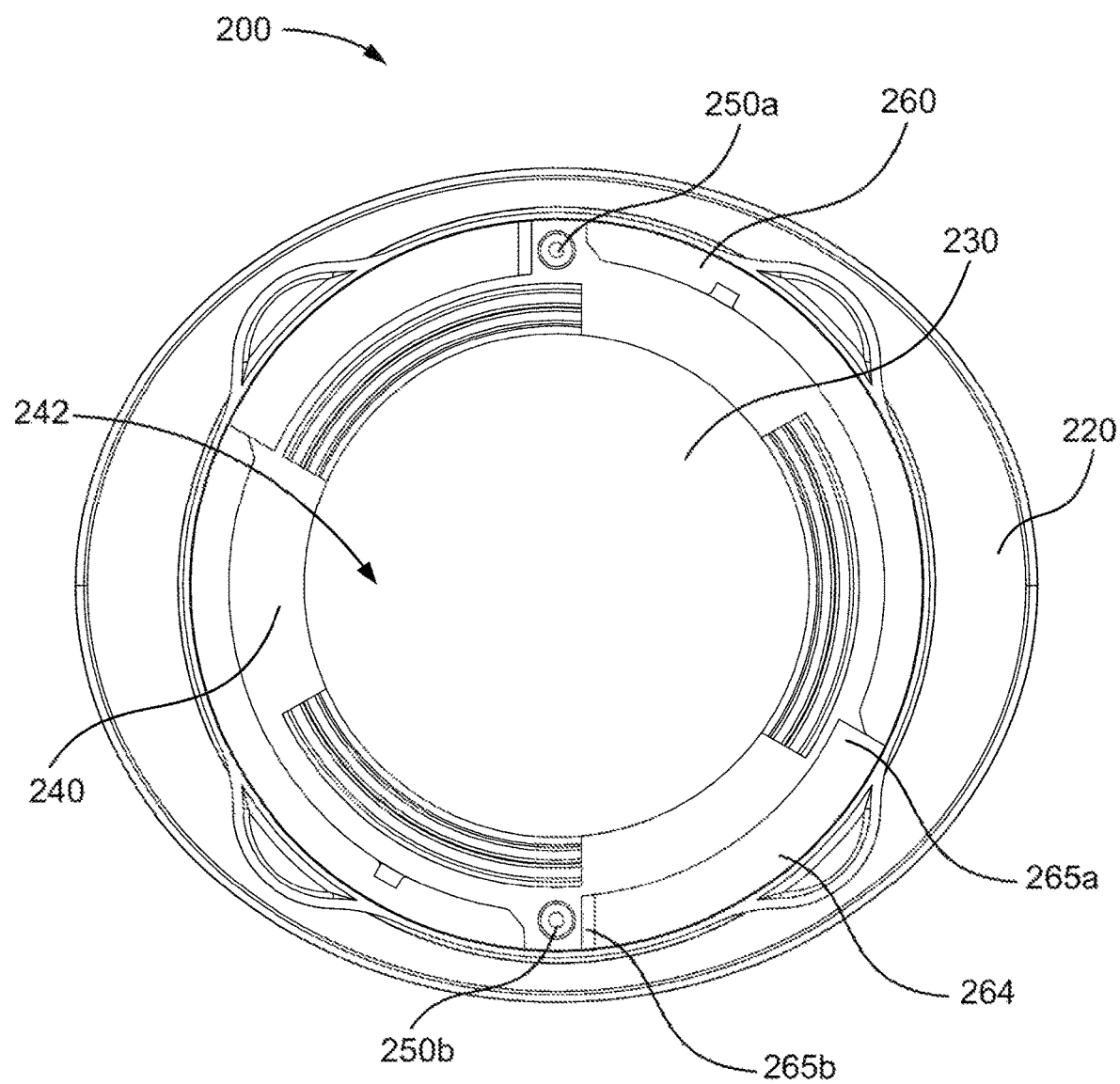
FIG. 4 is a bottom view of the sample container, according to an embodiment.

FIGS. 2-4 illustrate a sample container 200 according to an embodiment. As described above with reference to the sample container 100, the sample container 200 (also referred to herein as "specimen container" or "sample holder") is configured to hold an excised biological sample in a fixed position or a substantially fixed position so that examination and/or analysis can be performed after excision. In some embodiments, portions and/or aspects of the sample container 200 are substantially similar in form and/or function to the corresponding portions and/or aspects of the sample container 100 described above with reference to FIG. 1. Accordingly, such similar portions and/or aspects are not described in further detail herein.

As shown in FIG. 2, the sample container 200 includes a sample bag 210 defining an inner volume configured to receive a biological tissue sample, and a sealing member 220 coupled to the sample bag 210. A positioning member 240 is disposed against the sealing member 220 and substantially seals the inner volume. Referring now also to FIG. 3, an imaging window 230 is coupled to the positioning member 240 and is disposed and configured to be placed in contact with at least a portion of the biological sample. As described herein, the positioning member 240 can be coupled to and/or integrally formed with the imaging window 230. In some embodiments, the positioning member 240 can be non-uniformly shaped and the sealing member 220 can be dimensioned and configured such that the abutment of the sealing member 220 against the positioning member 240 can result in the sample container 200 being substantially sealed.

In some embodiments, the positioning member 240 defines the aperture 242 approximately in the center of the positioning member 240, and the imaging window 230 is disposed within the aperture 242. In some embodiments, the imaging window 230 is coupled to the positioning member 240 such that a substantially airtight seal is formed. In some embodiments, the positioning member 240, the imaging window 230, the sealing member 220, and the sample bag 210 collectively define the inner volume within which the biological sample is disposed during analysis.

As described herein, the positioning member 240 can be dimensioned and configured to abut a portion of an imaging device (not shown) to position the sample of biological tissue in three-dimensional space relative to a lens or probe of the imaging device. For example, as shown in FIGS. 3 and 4, the locking mechanism 260 includes a first channel 264 configured to retain the positioning member 240 in place. In some embodiments, the first channel 264 has a first end 265a and a second end 265b, the first end 265a being open and the second end 265b being substantially closed defining a first stop. In some embodiments, the first channel 264 is dimensioned and configured such that the positioning member 240 rotatably and lockably engages the imaging device.

In other words, in some embodiments the positioning member 240 can be connected to a receiving section of the imaging device in order for a ridge (not shown) or a thread (not shown) to fit into the channel 264. The positioning member 240 can then be rotated until either a) alignment markings are in alignment, b) until rotation is stopped by the ridge or thread coming to rest against the stop, c) a magnetic sensor senses the presence of the positioning member 240 and alignment thereof with regard to the receiving section of the imaging device, d) until the vacuum ports 250 are aligned with the vacuum system such that the vacuum system can draw air through the vacuum ports 250, or until some other approach terminates rotation or prompts a user (not shown) to stop rotating the positioning member 240. The user can then place the sealing member 220 onto the positioning member 240 and the biological tissue sample can then be positioned against the imaging window 230.

In some embodiments, a continuous vacuum system is configured such that the vacuum system automatically draws air from the sample container 200 once the first vacuum port 250a and/or second vacuum port 250b and any additional vacuum ports, collectively "vacuum ports 250" are aligned with the corresponding vacuum system ports on the imaging device. In some embodiments, the continuous vacuum system is a general vacuum system in the operating room or other clinical environment and is not a part of the imaging and/or analysis device. In some embodiments, a vacuum system remains off until such a time as the sample container 200 is in place for analysis and then initiates a vacuum pump or other vacuum device to withdraw air from the sample container 200. In some embodiments, the sample container 200 further includes a magnetic alignment device (not shown) that can detect when the vacuum ports 250 are aligned with the vacuum system ports. In some embodiments, the magnetic alignment device can alert the user when alignment is achieved. In some embodiments, the magnetic alignment device can be in communication with a processor and/or with the vacuum system such that when alignment between the vacuum ports 250 and vacuum system ports is achieved the vacuum system automatically begins pumping air from within the sample container 200. Once the vacuum system is initiated, air can be withdrawn from within the sample bag 210, the sample bag 210 being drawn down against the biological tissue sample, holding the biological tissue sample in a substantially fixed position.

Figure 5:
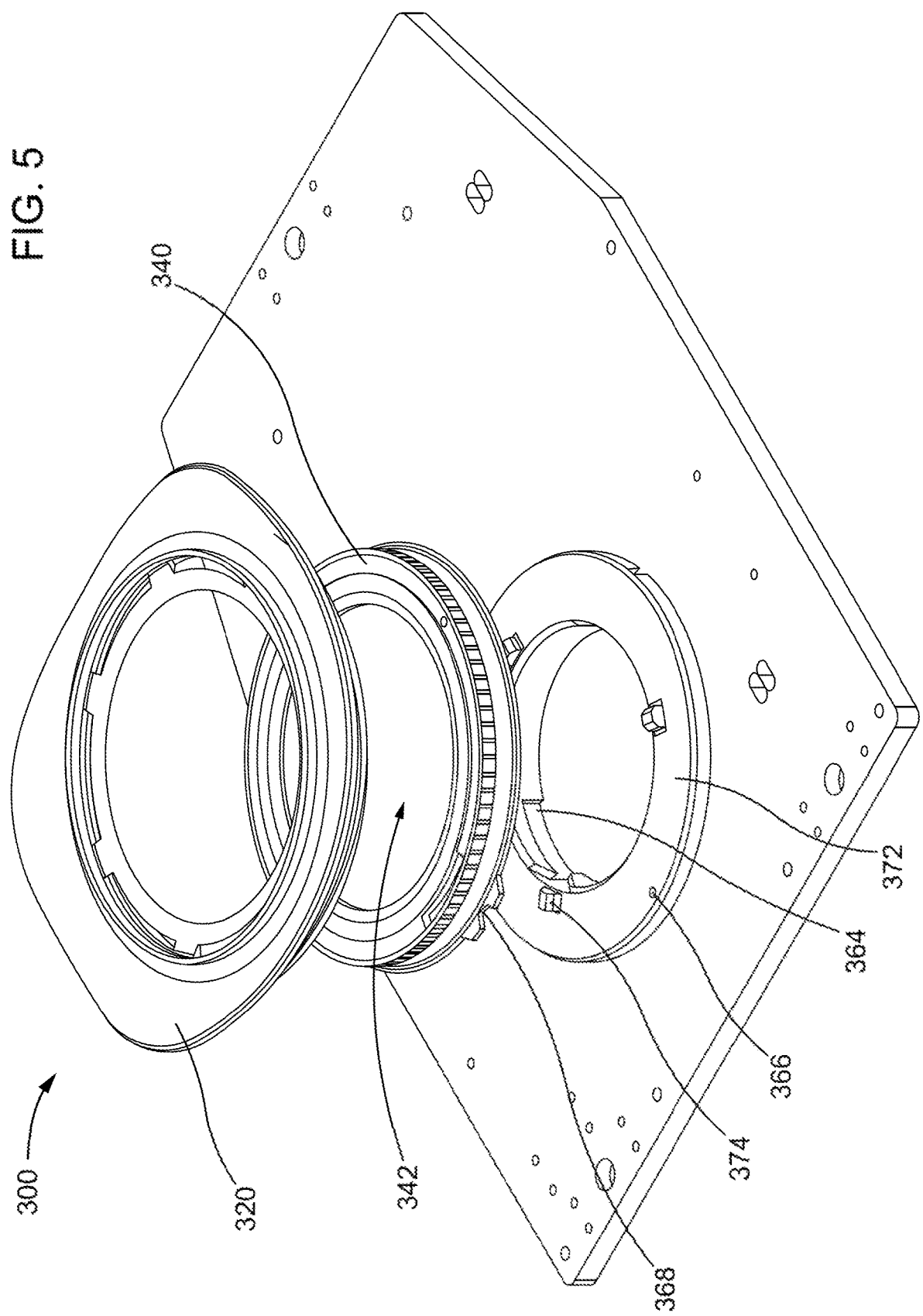
FIG. 5 shows an exploded view of a sample container, according to an embodiment.
Figure 6:
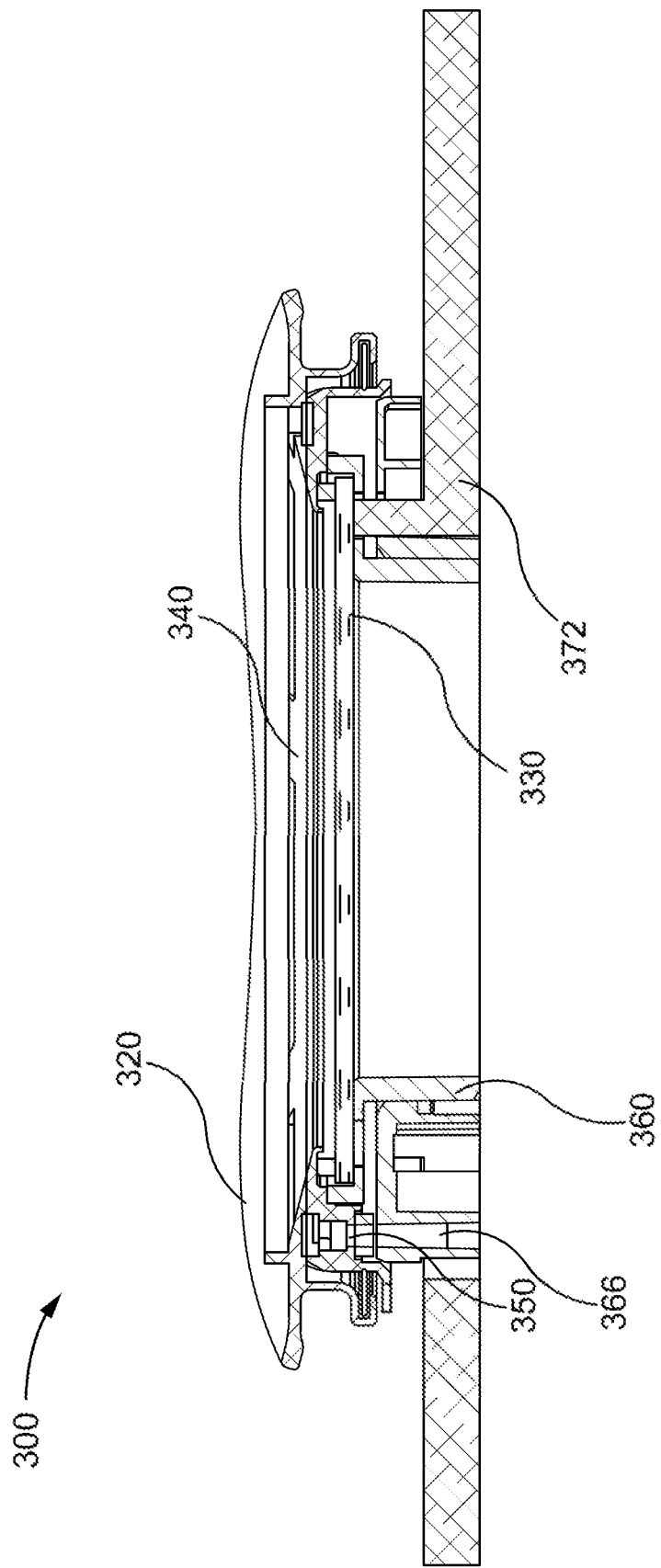
FIG. 6 shows a cross-section of the sample container of FIG. 5.

FIGS. 5 and 6 illustrate a sample container 300 according to an embodiment. As described above with reference to the sample container 100 and the sample container 200, the sample container 300 (also referred to herein as "specimen container" or "sample holder") is configured to hold an excised biological sample in a fixed position or a substantially fixed position so that examination and/or analysis can be performed after excision. In some embodiments, portions and/or aspects of the sample container 300 are substantially similar in form and/or function to the corresponding portions and/or aspects of the sample container 100 and or the sample container 200 described above with reference to FIGS. 1-4. Accordingly, such similar portions and/or aspects are not described in further detail herein.

The sample container 300 includes a sealing member 320, an imaging window 330, a positioning member 340, and a sample bag (not shown to more clearly convey the connection between the sealing member 320, the positioning member 340, and the imaging device). In some embodiments, the sample container 300 can be configured to be connected to the imaging device. In some embodiments, the imaging device includes a receiving member 372 dimensioned and configured to receive at least a portion of the sample container 300. In some embodiments, the receiving member 372 includes a channel 364 configured to receive a portion of the positioning member 340 in order to aid a user (not shown) in locking the positioning member 340 to the imaging device. In some embodiments, the receiving member 372 can include stops 374 that are dimensioned and configured to terminate rotation of the positioning member 340. In some embodiments, the stops 374 can be magnetized and/or electrically connected to an alignment monitoring system (not shown) which notifies the user when the stops 374 are contacted. In some embodiments, the alignment monitoring system is in communication with the vacuum system such that, once alignment is confirmed by the alignment monitoring system, the vacuum system is initiated and air is withdrawn from the sample bag, drawing the sample bag around a biological tissue sample (not shown).

In some embodiments, the positioning member 340 can include an alignment feature 368 that provides the user with a visual indication of alignment of the positioning member 340 with regard to the imaging device. In some embodiments, the alignment feature 368 is a tab that protrudes radially outward from the center of the positioning member 340 which indicates alignment of a vacuum port 350 with the vacuum system port 366.

In some embodiments, the sample container 300 can further include a locking mechanism 360 that holds the positioning member 340 in proper position, as shown in FIG. 6. Proper alignment of the positioning member 340 with respect to the imaging device can result in the vacuum port 350 being properly aligned above the vacuum system port 366, with very little or no clearance between the two ports. In some embodiments, the rotation of the positioning member 340 causes the engagement of the locking mechanism 360. In some embodiments, engaging the locking mechanism 360 moves the positioning member 340 closer towards the receiving member 372, causing the vertical gap between the vacuum port 350 and the vacuum system port 366 to close. This can help form a tight seal between the vacuum port 350 and vacuum system port 366 such that the vacuum system can better withdraw air from the sample bag.

Any of the sample containers 100, 200, 300, or 400 described herein (collectively "sample container") may be used to contain a biological tissue sample 402 during imaging and/or analysis. The sample container 400 may be used to provide a systematic means of communicating tissue sample orientation information relative to a reference point, such as on a patient's body for example, by using certain markers such as, but not limited to, radio opaque tags and imaging marking beads, for example. The sample container 400 may also be used to prevent sample mix-up and enforce a single-usage policy through the use of mechanical tabs and/or RFID tags, for example. The sample container 400, or a variant thereof, may also include a peel-off mechanism to expose a sterile portion of the sample container 400 that interfaces with a tissue handling system of the imaging system. For example, a portion of the sample container 400 may be initially covered by a material so that there is no direct contact between the operator and that portion of the sample container 400 during the loading and assembly of the sample container 400. The protected portion may then be exposed by peeling the protective material off of the sample container 400 prior to loading the container onto or into the imaging system. This may prevent blood or other fluids on the operator's gloves from being transferred into the scanning region of the imaging system. Furthermore, the sample container 400, or a variant embodiment thereof, may provide a means of trimming a guide wire prior to scanning. This may be realized by a detachable wire cutter mechanism resembling a nail trimmer that is packaged as an integral part of the sample container 400.

The sample container 400, and variants thereof, may provide safe and consistent handling of a tissue sample when attempting to image its entire surface. For example, the sample container 400 permits safe inversion of a contained tissue sample so that opposing surfaces can be imaged (or scanned). As another example, the sample container 400 may include orientation cues (or fiducials) that may permit consistent handling of the contained tissue sample by preserving the orientation of the contained tissue sample. In some embodiments, the contained tissue sample may be uniquely associated with particular patient information through the use of bar-codes and/or RFID tags applied to the sample container 400. This may provide a unique association between the patient information and the tissue sample that may reduce the mix-up of patient samples. In some example embodiments, the RFID tag or mechanical tabs can be further used to enforce single use of the sample container 400 so that the potential for cross-contamination of tissue samples is minimized. Finally, the sample container 400 may include an integrated trimmer tool that may be used to cut the guide wire, which is typically placed in a suspect region of the tissue sample as a pre-operative procedure, prior to imaging the tissue sample.

For example, one potential use scenario of the sample container 400 could involve placement of the biological tissue sample 402 in the sample container 400, scanning of the biological tissue sample 402 using OCT, transmission of the sample container 400 (still containing the biological tissue sample) to a radiology or MRI department, scanning of the sample container 400 using X-RAY or MRI while the biological tissue sample 402 is still in the sample container 400, and then the submerging of the biological tissue sample 402 in a preserving fluid such as formalin to preserve the biological tissue for longer-term storage. In some embodiments, the sample container 400 can be sealable, so the sample container 400 may allow the biological tissue sample 402 to be held in place within formalin until the biological tissue sample 402 is later imaged, stored or otherwise processed.

It should be noted that once the biological tissue sample 402 in the sample container 400 is scanned using another modality, in addition to OCT for example, the imaging data from the other modality could be co-registered with the OCT image data. In other words, one of the potential benefits of the sample containers disclosed herein, e.g., 100, 200, 300, and 400, is that is the comparability of imaging and analysis via different imaging devices, at different locations, and/or after an elapsed period of time. This is at least in part because the biological tissue sample 402 may be maintained in the same position, orientation and/or under the same compressive force (which can cause beneficial axial compression of the sample) when undergoing two or more different types of imaging or when imaging after an extended period. In other words, because the sample bag 410 and the imaging window 430 firmly engage the biological tissue sample 402 to keep the biological tissue sample 402 in place, the position and orientation repeatability between different analysis or imaging events can be maintained. In addition, since the imaging window 430 is sufficiently transparent for the different imaging modalities, the sample container 400 does not interfere with the various analysis or imaging events and the integrity of the various imaging and analysis results is maintained. In addition, because the orientation markers can be used to aid positioning of the sample container 400 with respect to the imaging device when using the different imaging modalities, the orientation markers being opaque to these imaging modalities, the sample container 400 can be consistently positioned with respect to the imaging device leading to more consistent results. A user 480 could then view the two images on the same interface. For example, if the sample container 400 underwent X-ray imaging after OCT imaging, the user 480 could view the radiograph information alongside the OCT image data in the same interface and infer characteristic information about the excised biological tissue sample 402 from both imaging results without being required to consider position, orientation, and/or sample shape changes between imaging modalities. Alternatively, if the other modality is MRI Imaging, then hi-resolution data for the surface of the MRI image could be obtained by overlaying the OCT image data on the MRI image data. It should be noted that this technique may be used with the other embodiments of the sample container 400 described herein.

For many imaging and/or analysis techniques, the biological tissue sample 402 should be positioned very precisely to facilitate accurate analysis/imaging. For instance, OCT imaging uses near-infrared light to produce high-resolution images of various objects such as, but not limited to tissue, for example. When OCT imaging is used on tissue, it is analogous to high-frequency ultrasound, except that the optical interferometry of OCT imaging is used for depth ranging rather than echo timing. OCT imaging is rapid, non-contact, non-invasive, and capable of generating 2D and 3D images at high resolution (~10 μm). In OCT imaging, the registration of the imaging window 430 can be important because the OCT image has micron level resolution and a shallow depth of field. This means the imaging window 430 should be positioned with a high level of accuracy relative to the imaging plane. Therefore, in some embodiments, the sample container 400 and/or the imaging device can include spacers and/or raised surfaces that result in the imaging window 430 being placed into a precise position once a positioning member 440 is disposed to the imaging device.

In addition, for many of the imaging and/or analysis techniques typically used to examine the excised biological tissue sample 402, the biological tissue sample 402 should remain substantially motionless during the analysis/imaging period. After excitation of the biological tissue sample 402, especially if the tissue sample is not cleaned and/or dried before analysis, can be quite slippery and therefore difficult to handle during imaging and/or analysis. A practitioner holding the biological tissue sample 402 can often find it difficult to keep the sample in a particular location during imaging and/or analysis. The use of compression plates to hold the excised biological tissue sample 402 in place for imaging and/or analysis has been tried, however, the flat surface of the compression plates are typically unable to contain the slippery specimen. Therefore, it can be especially important to have a particularly contoured surface that contacts and holds the biological tissue sample 402 in place during analysis/imaging. A molded contact surface, however, is molded for a particular excised biological tissue sample 402 and may not be useful for specimens of different size and/or shape. Therefore, using the sample bag 410 as a contacting surface for the biological tissue sample 402 can increase the ease with which the biological tissue sample 402 is held substantially motionless during analysis/imaging.

In some embodiments, the sample bag 410 can have a first configuration in which the sample bag 410 is fully expanded such that the inner volume is maximized and a second configuration in which the sample bag 410 is drawn substantially tightly around the biological tissue sample 402 such that the inner volume is minimized. In some embodiments, the biological tissue sample 402 can be disposed within the sample container 400 immediately after excision of the biological tissue sample 402 from the patient. In some embodiments, the sample container 400 can be positioned in close proximity to the location where surgical excision of the biological tissue sample 402 takes place such that the biological tissue sample 402 can be easily and quickly disposed within the sample container 400, the sample container 400 containing the biological tissue sample 402 then being transported to the imaging device for analysis. In some embodiments, the imaging device can also be positioned in close proximity to the location where surgical excision of the biological tissue sample 402 takes place. In some embodiments, the imaging device is in a third location outside of the location where surgical excision of the biological tissue sample 402 takes place. In other words, the sample container 400 can be used to hold the biological tissue sample 402 during analysis, can be used to transport the biological tissue sample 402 from the surgical facility to a separate facility for analysis, and/or can be used to store the biological tissue sample 402 for a period of time.

FIGS. 7A-7E show a method by which a biological tissue sample can be disposed within a sample container, e.g., the sample container 400. FIGS. 8-13 illustrate a method for holding a biological tissue sample in a substantially fixed position using a sample container, e.g., the sample container 400. While FIGS. 7A-7E illustrate the method using the sample container 400, any of the sample containers described herein (e.g., 100, 200, 300, or the like) could be used according to the methods described herein.

Figure 7A:
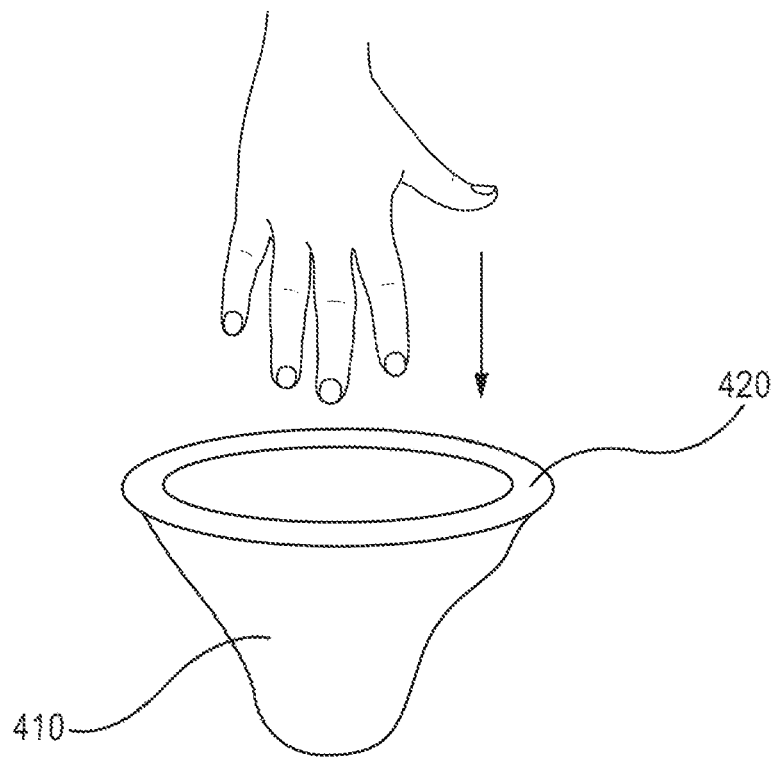
FIGS. 7A-7E show a method for holding a biological tissue sample in a substantially fixed position, according to an embodiment.
Figure 7B:
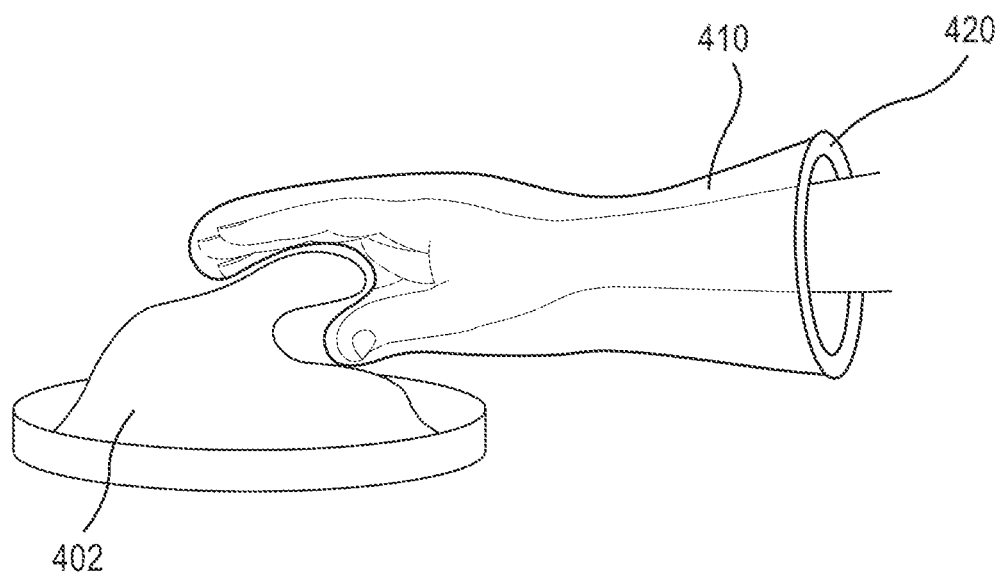
Figure 7C:
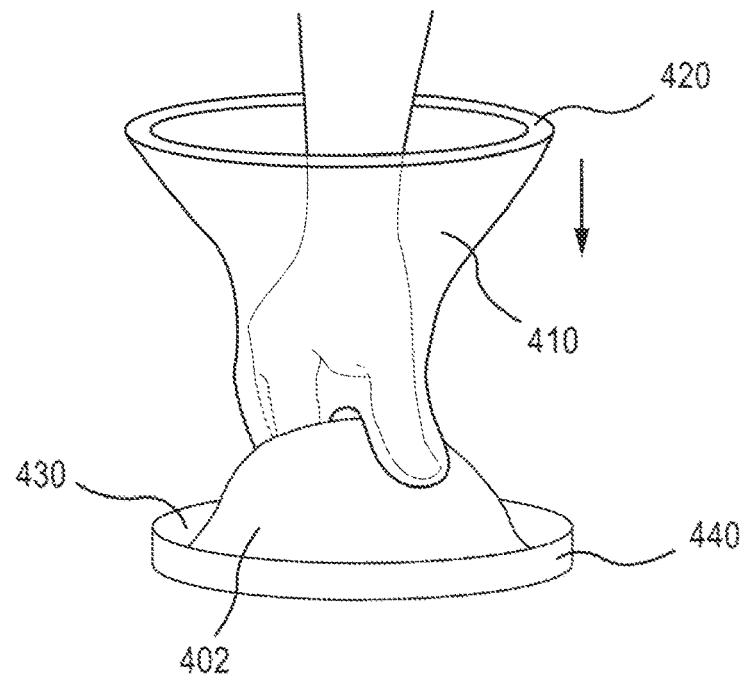
Figure 7D:
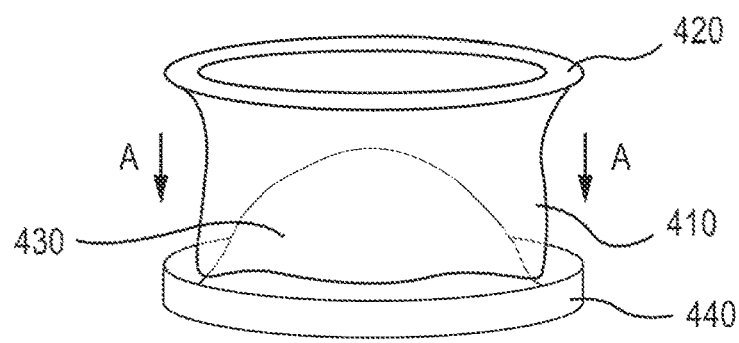
Figure 7E:
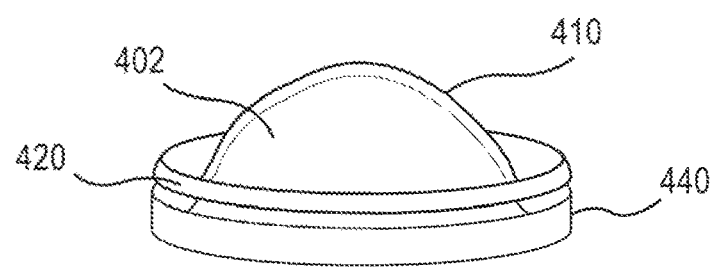

The sample container 400 is configured to hold an excised biological sample 402 in a fixed position or a substantially fixed position so that examination and/or analysis can be performed after excision. As shown in FIG. 7A, in order to dispose the biological tissue sample 402 within the sample bag 410, the user 480 can invert the sample bag 410 and insert their hand through a sealing member 420 into the sample bag 410, thus handling the biological tissue sample 402 with hands covered by the inverted sample bag 410. As shown in FIG. 7B, the user 480 can then dispose the biological tissue sample 402 within the sample bag 410. As shown in FIG. 7C, the user 480 can then place the biological tissue sample 402 onto an imaging window 430 coupled to the positioning member 440. As shown in FIG. 7D, the user 480 can then restore the sample bag 410 to its proper, non-inverted configuration and move the sealing member 420 down around the biological tissue sample 402. As shown in FIG. 7E, the user 480 can then position the sealing member 420 against the positioning member 440 to seal the biological tissue sample 402 in the sample bag 410. In some embodiments, the user 480 can activate a vacuum system (not shown) to evacuate air from the sample bag 410, thereby drawing the sample bag 410 into close proximity to the biological tissue sample 402. As the sample bag 410 is drawn into contact with the biological tissue sample 402, the sample container 400 can be used to maintain the biological tissue sample 402 in a proper position for imaging and/or analysis. In some embodiments, the vacuum system used is a general vacuum system within an operating room or other clinical or surgical environment. In some embodiments, the vacuum system is automatically activated once alignment of the vacuum ports with the device vacuum ports is achieved. In some embodiments, the vacuum system can be connected to the sample container 400 before the sample container is positioned within or upon the imaging device. In other words, the vacuum system can be connected to the sample container, air withdrawn from within the sample container, then valves configured to be closed in order for the sample container to be sealed, and finally the sample container positioned for imaging of the biological tissue sample 402.

FIGS. 8-12 illustrate a method for holding a biological tissue sample in a substantially fixed position using a sample container, e.g., the sample container 400. While FIGS. 8-12 illustrate the method using the sample container 400, any of the sample containers described herein (e.g., 100, 200, 300, or the like) could be used according to the methods described herein.

Figure 8:
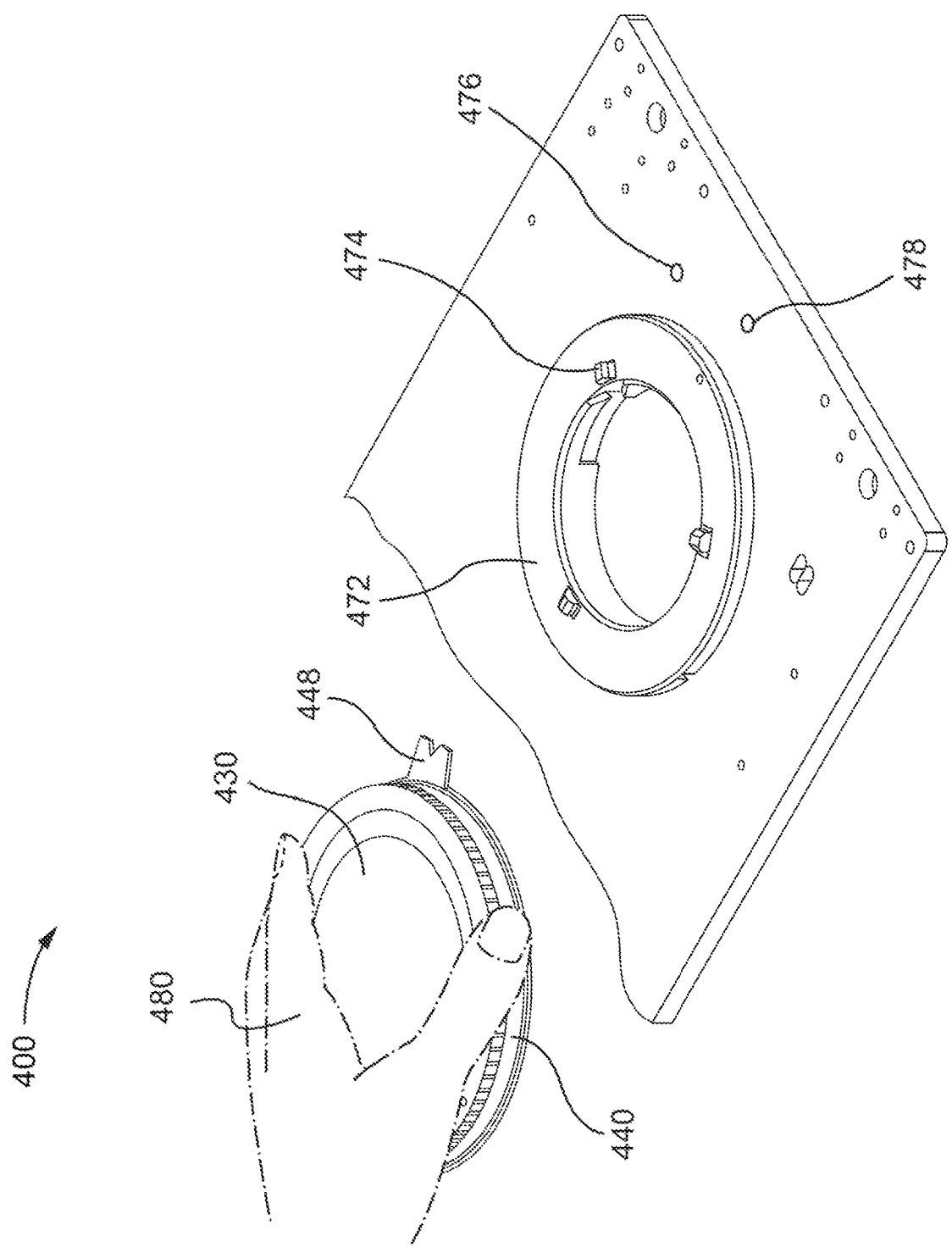
FIGS. 8-12 show a method for holding a biological tissue sample in a substantially fixed position, according to an embodiment.
Figure 9:
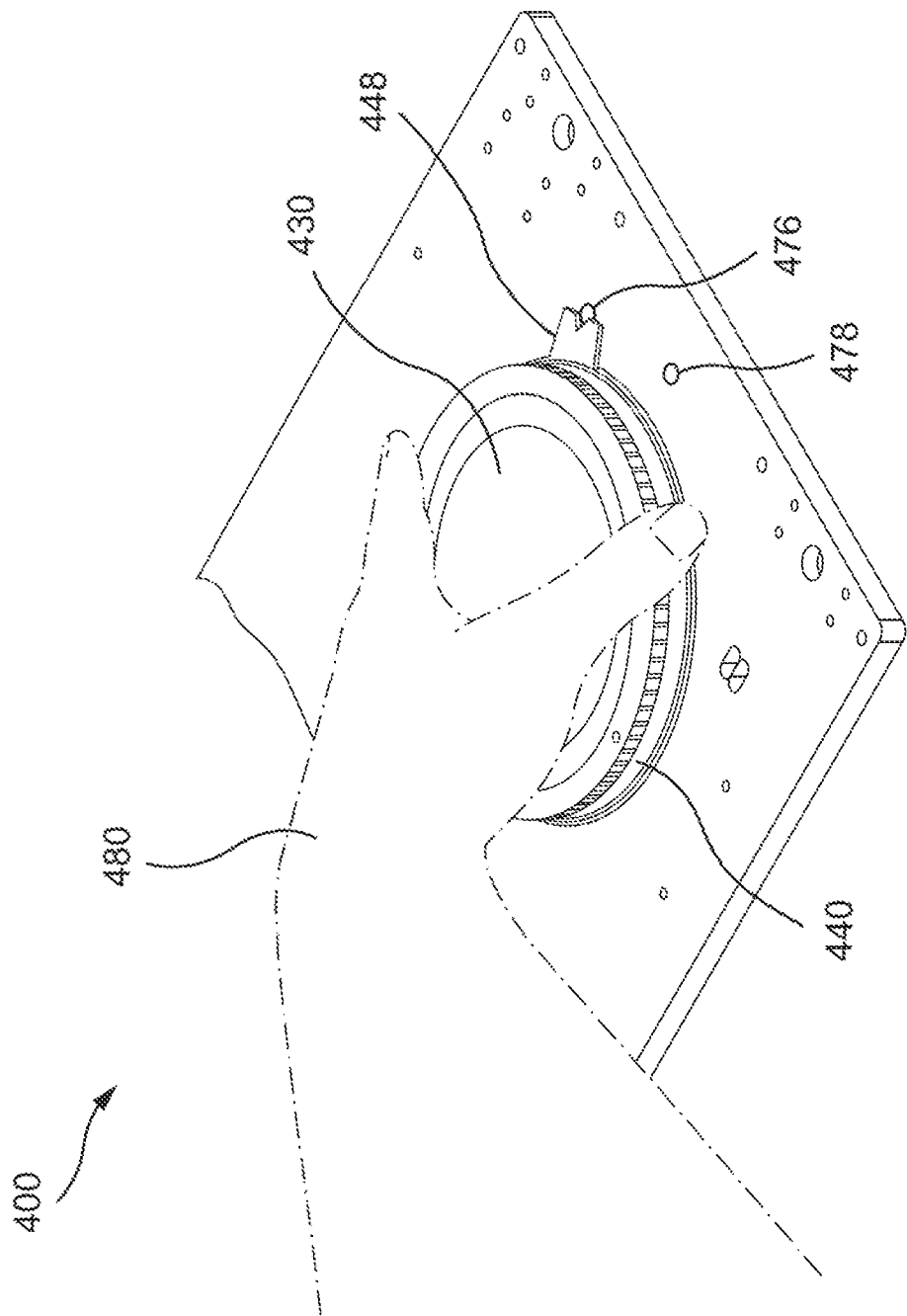

As shown in FIG. 8, in order to position a biological tissue sample 402 precisely for imaging using the sample container 400, a user 480 can first move the positioning member 440 into place above a receiving member 472. In some embodiments, the positioning member 440 can have an alignment feature 448. When the positioning member 440 is disposed against the receiving member 472, as shown in FIG. 9, the user 480 can position the sample container 400 such that the alignment feature 448 aligns with a first alignment marking 476. Alignment of the alignment feature 448 with the first alignment marking 476 indicates to the user 480 that the positioning member 440 can be fitted into the receiving member 472 and rotated to lock the positioning member 440 into place.

Figure 10:
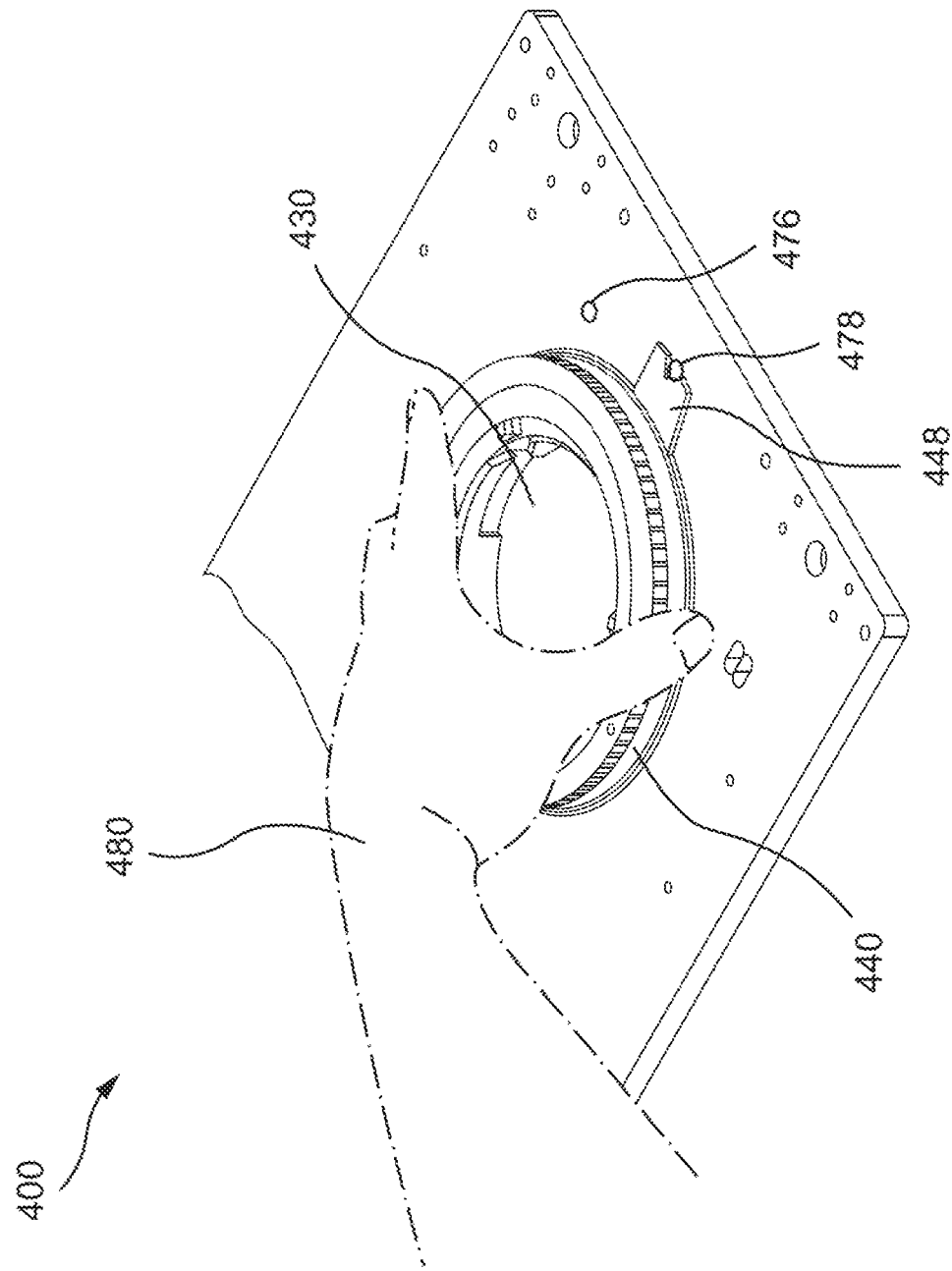

As shown in FIG. 10, the user 480 then rotates the positioning member 440 until the alignment feature 448 aligns with a second alignment marking 478, indicating to the user 480 that a vacuum port (not shown) is properly aligned with a vacuum system port (not shown). In some embodiments, the receiving member 472 includes a stop 474. In some embodiments, the stop 474 is positioned such that when the positioning member 440 is disposed to the receiving member 472 the stop 474 arrests vertical, horizontal, and/or rotational motion. In some embodiments, the dimensions and configuration of the stops 474 are such that the imaging window 430 is positioned at a precise distance above an imaging/analysis probe and/or lens and/or discharge point once the rotational and/or vertical motion of the positioning member 440 is arrested by the stop 474.

In some embodiments, the positioning member 440 and/or receiving member 472 include a magnetic alignment device (not shown) or components thereof. In some embodiments, the magnetic alignment device can be a sensor attached on the receiving member 472 that is connected to a processor, the sensor configured to detect the presence of a magnet at a corresponding location on the positioning member 440, indicating alignment of the vacuum port with the vacuum system port. In some embodiments, the magnetic alignment device is connected to a light, a sounding device, or another alert system such that an indication of alignment can be communicated to the user 480 when attaching the positioning member 440 to the receiving member 472. In some embodiments, the sensor can be connected to a circuit such that when the sensor senses that the positioning member 440 is aligned within the receiving member 472, a circuit is closed and electrical current is allowed to be supplied to the light, the sounding device (auditory alarm), or other alert system. In some embodiments, the magnetic alignment device is also connected to the vacuum system such that when alignment is confirmed by the magnetic alignment device the vacuum system is initiated automatically in response.

Figure 11:
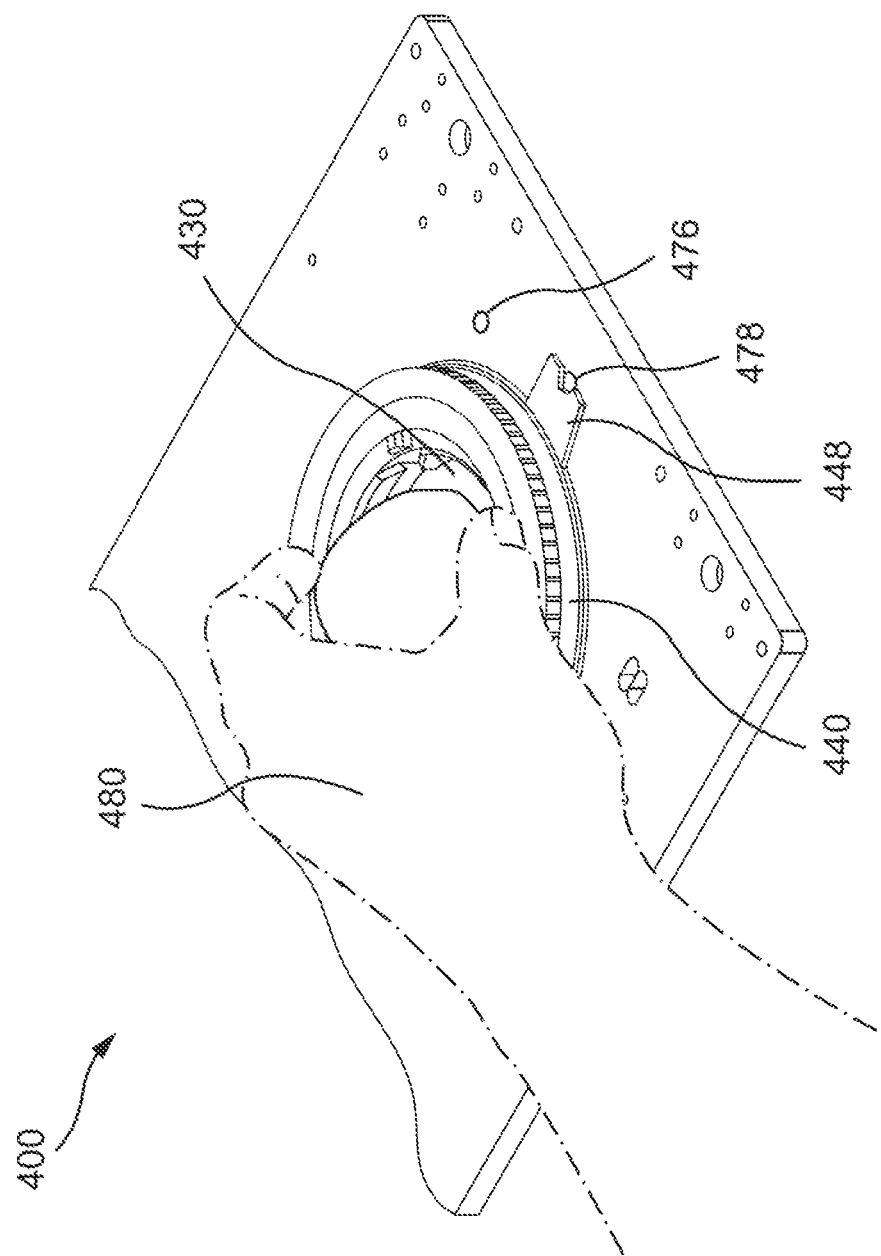

Once the positioning member 440 is positioned and/or locked against the receiving member 472 or directly against the imaging device, the user 480 can place the biological tissue sample 402 onto the imaging window 430, as shown in FIG. 11. In some embodiments, the user 480 can dispose the biological tissue sample 402 into the sample bag 410 and subsequently invert the sample bag 410, disposing the biological tissue sample 402 onto the imaging window 430, instead of the user 480 disposing the biological tissue sample 402 directly onto the imaging window 430.

Figure 12:
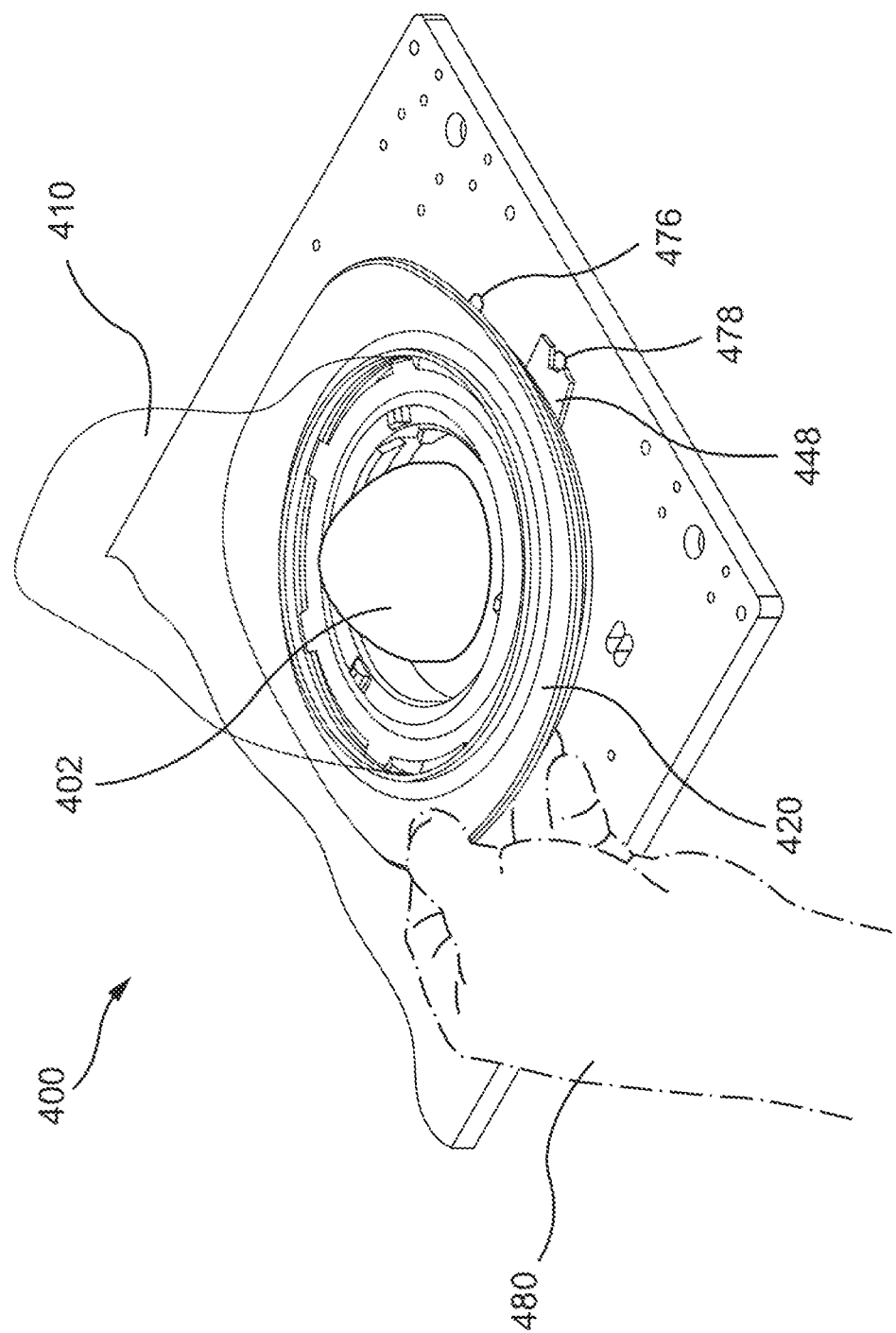

Once the user 480 disposes the biological tissue sample 402 against the sample window 430, the sealing member 420, being coupled to the sample bag 410, can be placed on top of the positioning member 440 such that the biological tissue sample 402 is substantially covered by the sample bag 410, as shown in FIG. 12. In some embodiments, the sealing member 420 is placed on top of the positioning member 440 and held in place by the user 480. The user 480 can place one or both hands over the sealing member 420 and apply pressure against the positioning member 440 for the duration of imaging/analysis. In some embodiments, the sealing member 420, to which the sample bag 410 is attached, can be placed on top of the positioning member 440 and a seal maintained by the withdrawal of air from within the sample bag 410 by the vacuum system. In some embodiments, when the vacuum system is not initiated and air is not being withdrawn from the sample bag 410, the sample bag 410 maintains the first configuration wherein it is generally expanded. In some embodiments, when the vacuum is initiated and air is being withdrawn from the sample bag 410, the sample bag 410 transitions to the second configuration wherein it is substantially tightly drawn about the biological tissue sample 402. In some embodiments, when the sample bag 410 maintains the second configuration, the biological tissue sample 402 is held substantially immobile and maintains a fixed position or a substantially fixed position, facilitating more accurate and more rapid imaging and/or analysis by the user 480.

Figure 13:
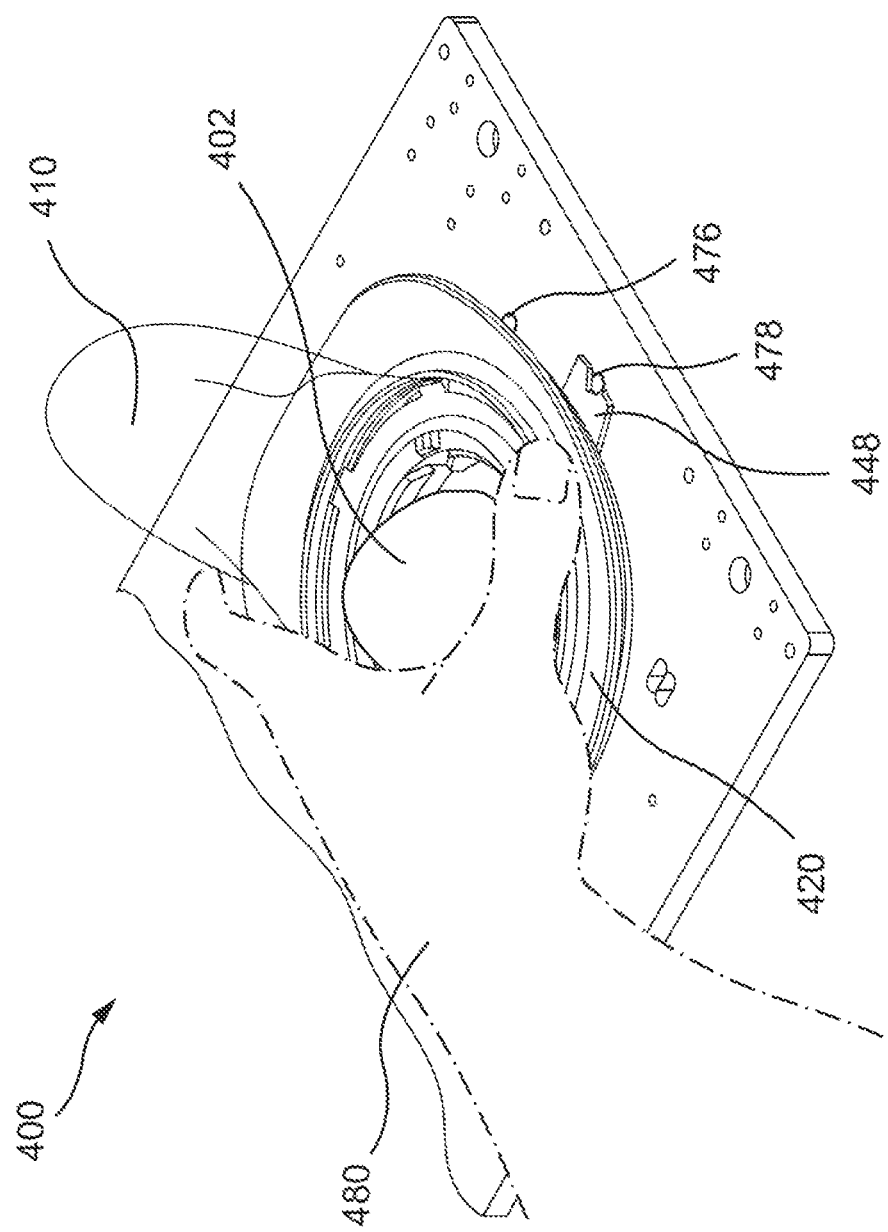
FIG. 13 shows a method for holding a biological tissue sample in a substantially fixed position, according to an embodiment.

FIG. 13 illustrates a method for holding a biological tissue sample in a substantially fixed position 10, e.g., during imaging and/or storage. The method 10 includes receiving a biological tissue sample into an inner volume of a sample bag, the sample bag coupled to a sealing member, at 11. In some embodiments, a user (e.g., a laboratory technician, an imaging technician, a nurse, a surgeon, or any other user) can dispose the biological tissue sample into the sample bag. In some embodiments, the user can invert the sample bag, grasp the biological tissue sample with the inverted bag, and revert the sample bag such that the biological tissue sample remains within the sample bag. In some embodiments, the sample bag can be disposed in an uncompressed, rolled, non-deformed or otherwise flat configuration flush with a conventional operating room surface or laboratory surface. For instance, the sample bag can initially include a receiving tip portion and a rolled sheath portion. In some embodiments, the receiving portion of the sample bag can be configured to receive the biological tissue sample and the rolled sheath portion can be configured to be unrolled to cover the biological tissue sample once the biological tissue sample is disposed onto the receiving portion of the sample bag.

The method 10 includes disposing an imaging window into contact with a portion of the biological tissue sample, at 12. In some embodiments, the imaging window can be coupled to the sealing member such that the imaging window substantially spans the opening of the sample bag, sealing the biological tissue sample within the inner volume defined by the sample bag and the imaging window. In some embodiments, the imaging window can be slidably disposed within a portion of the sealing member. In some embodiments, the imaging window can be rotatably disposed within the sealing member, for instance around a point along an edge or circumference of the imaging window.

The method 10 optionally includes coupling a positioning member to the imaging window to form a sample container such that the biological tissue sample is substantially sealed within the sample container, at 13. In some embodiments, the positioning member can include the imaging window such that the method does require the positioning member to be coupled to the imaging window. In some embodiments, the imaging window can be fused, clamped, soldered, glued, adhered, taped, screwed, nailed, stapled, or coupled to the positioning member. In some embodiments, the imaging window can be coupled to the positioning member such that once the sample container is fully assembled, no or substantially no air leaks occur between the positioning member and the imaging window. In some embodiments, the positioning member can include a centered aperture and a surround. In some embodiments, the surround can include a lip on which at least a portion of the imaging window is disposed such that the imaging window spans or substantially spans the centered aperture. In some embodiments, the lip can include a deformable sealing member onto which the portion of the imaging window can be disposed such that an airtight or substantially airtight seal is formed between the deformable sealing member and the imaging window. In some embodiments, the lip can be positioned on a bottom side of the surround such that the imaging window can be disposed between the positioning member and a receiving member of an imaging device. In some embodiments, the lip can be positioned on a top side of the surround such that the imaging window can be disposed between the positioning member and the sealing member. In some embodiments, the positioning member can include two parts, e.g., two halves, configured to fit together to form the positioning member. In some embodiments, the lip can be positioned on an inside of one of the two parts of the positioning member such that the imaging window can be interposed between the two parts, the two parts can then be coupled together to form the positioning member, and the imaging window can span or substantially span the positioning member.

The method 10 optionally includes interposing the sealing member between the positioning member and a locking mechanism, the locking mechanism including a channel configured to lockably engage a portion of the positioning member, at 14. In some embodiments, the locking mechanism can be integral to the positing member. In some embodiments, the locking mechanism can be a separate component configured to be disposed about, over, or nearby the positioning member and to lockably engage a protrusion of the positioning member, the protrusion dimensioned and configured to lockably engage the channel to stop rotational, vertical, and/or horizontal motion of the positioning member. In some embodiments, the protrusion can be a ridge or a plurality of ridges positioned about the surround of the positioning member.

The method 10 includes removably locking the sample container to a receiving member, at 15. In some embodiments, the sample container can be rotatably locked to the receiving member. In some embodiments, the receiving member can include a receiving aperture configured and dimensioned to receive the positioning member or a portion thereof. In some embodiments, the receiving aperture can define a wall or a plurality of walls or a circular channel having an inner surface. In some embodiments, the wall or plurality of walls or inner surface of the circular channel can include a channel. In some embodiments, the positioning member can have a bottom side that includes one or more protrusions configured to fit fixedly into the channel within the aperture of the receiving member to retain the sample container in place relative to the imaging device. In some embodiments, when the positioning member is rotated into a locking position within the aperture of the receiving member or otherwise positioned fixedly with respect to the imaging device, a vacuum port or a plurality of vacuum ports within the positioning member, the vacuum ports being configured to pass therethrough into the inner volume of the sample bag, can be aligned or substantially aligned with a vacuum system, e.g., of the imaging device. In some embodiments, when the vacuum ports are aligned with the vacuum system, a flow path or a plurality of flow paths are defined between the vacuum system and the inner volume of the sample bag.

The method 10 includes withdrawing air from the inner volume of the sample bag, at 16. In some embodiments, a portion of the air within the sample bag can be withdrawn. In some embodiments, all or substantially all of the air within the sample bag can be withdrawn. In some embodiments, by removing air from within the sample bag, the sample container being airtight or substantially airtight, the sample bag can be drawn closer about the biological tissue sample. In some embodiments, the vacuum system can be a continuous vacuum system configured such that the vacuum system automatically draws air from the sample container once the vacuum port or plurality of vacuum ports are aligned with the corresponding vacuum system ports on the imaging device. In some embodiments, the continuous vacuum system is a general vacuum system in the operating room or other clinical environment and is not a part of the imaging and/or analysis device. In some embodiments, a vacuum system remains off until such a time as the sample container is in place for analysis and then initiates a vacuum pump or other vacuum device to withdraw air from the sample container. In some embodiments, the sample container further includes a magnetic alignment device (not shown) that can detect when the vacuum ports are aligned with the vacuum system ports. In some embodiments, the magnetic alignment device can alert the user when alignment is achieved. In some embodiments, the magnetic alignment device can be in communication with a processor and/or with the vacuum system such that when alignment between the vacuum ports and vacuum system ports is achieved the vacuum system automatically begins pumping air from within the sample container. Once the vacuum system is initiated, air can be withdrawn from within the sample bag, the sample bag being drawn down against the biological tissue sample, holding the biological tissue sample in a substantially fixed position. In some embodiments, the sample bag can apply some compressive force to the biological tissue sample such that the biological tissue sample can be deformed in a controlled and non-destructive manner. In some embodiments, deformation of the biological tissue sample can include a lateral deformation of the biological tissue sample such that the biological tissue sample is lies flatter on the imaging window and so that more of the biological tissue sample can be sampled in a single positioning of the biological tissue sample. In some embodiments, for example in order to conduct margin analysis of an excised tumor or other potentially malignant biological tissue sample, the vacuum system can be disengaged after initial imaging of the sample. In some embodiments, once the vacuum system is disengaged, the sample bag can be loosened from about the biological tissue sample and the biological tissue sample can be repositioned (e.g., flipped over a horizontal axis), the vacuum system can be re-engaged to drawn the sample bag about the repositioned biological tissue sample, and secondary imaging can be conducted. In some embodiments, however, by drawing the sample bag about the biological tissue sample such that the sample bag applied at least some compressive force and so that the biological tissue sample is at least partially deformed, less repositioning of the biological tissue sample may be necessary.

To provide an overall understanding, certain illustrative embodiments have been described; however, it will be understood by one of ordinary skill in the art that the systems, apparatuses, and methods described herein can be adapted and modified to provide systems, apparatuses, and methods for other suitable applications and that other additions and modifications can be made without departing from the scope of the systems, apparatuses, and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems, apparatuses, or methods of the present disclosure.

The embodiments have been particularly shown and described, but it will be understood that various changes in form and details may be made.

Conventional terms in the field of medical devices have been used herein. The terms are known in the art and are provided only as a non-limiting example for convenience purposes. Accordingly, the interpretation of the corresponding terms in the claims, unless stated otherwise, is not limited to any particular definition. Thus, the terms used in the claims should be given their broadest reasonable interpretation.

Although specific embodiments have been illustrated and described herein, it will be appreciated by those of ordinary skill in the art that any arrangement that is adapted to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "imaging" or "analysis" are used interchangeably here and are not to be considered limiting in any way. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure and is submitted with the understanding that it will not be used to interpret or limit the scope or meaning of the claims.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

The invention claimed is:

1. An apparatus for holding a biological tissue sample in a substantially fixed position, the apparatus comprising:
   a sample bag defining an inner volume configured to receive the biological tissue sample;
   a sealing member coupled to the sample bag;
   an imaging window substantially spanning the opening of the sample bag and
   configured to be placed in contact with at least a portion of the biological tissue sample; and
   a positioning member coupled to the imaging window and configured to be disposed against the sealing member, the positioning member including a vacuum port disposed and configured to be aligned with a vacuum source to withdraw air from the inner volume of the sample bag.

2. The apparatus of claim 1, wherein the inner volume is substantially sealed when the positioning member is disposed against the sealing member.

3. The apparatus of claim 1, further comprising:
   a receiving member having a channel to which a portion of the positioning member is configured to be disposed, the channel defined at least in part by a first wall spaced a distance from a second wall.

4. The apparatus of claim 3, further comprising:
a locking mechanism configured to retain the portion of the positioning member disposed within the channel of the receiving member.

5. The apparatus of claim 4, wherein the locking mechanism includes a ridge configured to have a shape and a volume substantially similar to a shape and a volume of the channel.

6. The apparatus of claim 3, wherein the channel has a first end that is substantially open and a second end that is substantially closed.

7. The apparatus of claim 6, wherein further motion of the positioning member is disallowed once a distal end of the portion of the positioning member abuts the substantially closed second end of the channel.

8. The apparatus of claim 3, further comprising:
a plurality of registration points disposed about the receiving member and configured to arrest movement of the positioning member once a portion of the positioning member is disposed within the channel.

9. The apparatus of claim 3, wherein the receiving member is configured to be coupled to an imaging device such that the biological tissue sample is securely positioned against the sample window and readily available for analysis.

10. The apparatus of claim 3, wherein analysis includes the communication of electromagnetic energy from the imaging device, through the sample window, to the biological tissue sample.

11. The apparatus of claim 3, further comprising:
an alignment element connected to the positioning member;
a first alignment marking indicating the first end of the channel; and
a second alignment marking indicating the second end of the channel.

12. The apparatus of claim 11, wherein the alignment element is configured to move between the first alignment marking and the second alignment marking as the positioning member is rotationally connected to an imaging device.

13. The apparatus of claim 12, wherein alignment between the alignment element and the second alignment marking indicates proper alignment of the vacuum port with the vacuum System.

14. The apparatus of claim 11, further comprising:
an electronic sensor configured to close a circuit when the vacuum port is properly aligned with the vacuum system; and
an indicator light connected to the circuit and configured to illuminate when the circuit is closed.

15. The apparatus of claim 11, further comprising:
an electronic sensor configured to close a circuit when the vacuum port is properly aligned with the vacuum system; and
an audible alarm connected to the circuit and configured to produce a sound when the circuit is closed.

16. The apparatus of claim 1, wherein the positioning member includes a first portion and a second portion, the sealing member disposed between the first portion and the second portion such that the inner volume is substantially sealed.

17. The apparatus of claim 1, wherein at least one of the sample bag, the sealing member, the imaging window, and the positioning member is reusable.

18. The apparatus of claim 17, wherein at least one of the sample bag, the sealing member, the imaging window, and the positioning member is configured to be sterilized in an autoclave before reuse.

19. The apparatus of claim 1, wherein the vacuum source is a vacuum pump.

20. The apparatus of claim 1, wherein the vacuum port can be sealed such that a partial vacuum can be maintained within the apparatus once the vacuum source is disconnected.

21. An apparatus for holding a biological tissue sample in a substantially fixed position, the apparatus comprising:
a sample bag having an opening and defining an inner volume, the sample bag configured to receive the biological tissue sample and having a first inner volume in a first configuration and a second inner volume less than the first inner volume in a second configuration;
a sealing member coupled to a circumference of the opening of the sample bag;
an imaging window substantially spanning the opening of the sample bag and
configured to be placed in contact with a portion of the biological tissue sample; and
a positioning member coupled to the imaging window and configured to be disposed against the sealing member, the positioning member including a vacuum port disposed and configured to be aligned with a vacuum source to withdraw air from the inner volume of the sample bag,
wherein withdrawing air from the inner volume of the sample bag moves the sample bag from the first configuration to the second configuration.

22. The apparatus of claim 21, wherein the sample bag is substantially airtight when the positioning member is disposed against the sealing member.

23. The apparatus of claim 22, wherein the sample bag is configured to be disposed tightly about the biological tissue sample in the second configuration such that the biological tissue sample is held in the substantially fixed position.

24. The apparatus of claim 21, further comprising:
a receiving member having a channel to which a portion of the positioning member is configured to be disposed, the channel defined at least in part by a first wall spaced a distance from a second wall.

25. The apparatus of claim 24, further comprising:
a locking mechanism configured to retain the portion of the positioning member disposed within the channel of the receiving member.

26. The apparatus of claim 25, wherein the locking mechanism includes a ridge configured to have a shape and a volume substantially similar to a shape and a volume of the channel.

27. The apparatus of claim 24, wherein the channel has a first end that is substantially open and a second end that is substantially closed.

28. The apparatus of claim 27, wherein further motion of the positioning member is disallowed once a distal end of the portion of the positioning member abuts the substantially closed second end of the channel.

29. The apparatus of claim 24, further comprising:
a plurality of registration points disposed about the receiving member and configured to arrest movement of the positioning member once a portion of the positioning member is disposed within the channel.

30. The apparatus of claim 24, wherein the receiving member is configured to be coupled to an imaging device such that the biological tissue sample is securely positioned against the sample window and readily available for analysis.

31. The apparatus of claim 24, wherein analysis includes the communication of electromagnetic energy from the imaging device, through the sample window, to the biological tissue sample.

32. The apparatus of claim 24, further comprising:
an alignment element connected to the positioning member;
a first alignment marking indicating the first end of the channel; and
a second alignment marking indicating the second end of the channel.

33. The apparatus of claim 32, wherein the alignment element is configured to move between the first alignment marking and the second alignment marking as the positioning member is rotationally connected to an imaging device.

34. The apparatus of claim 33, wherein alignment between the alignment element and the second alignment marking indicates proper alignment of the vacuum port with the vacuum system.

35. The apparatus of claim 32, further comprising:
an electronic sensor configured to close a circuit when the vacuum port is properly aligned with the vacuum system; and
an indicator light connected to the circuit and configured to illuminate when the circuit is closed.

36. The apparatus of claim 32, further comprising:
an electronic sensor configured to close a circuit when the vacuum port is properly aligned with the vacuum system; and
an audible alarm connected to the circuit and configured to produce a sound when the circuit is closed.

37. The apparatus of claim 21, wherein the positioning member includes a first portion and a second portion, the sealing member disposed between the first portion and the second portion such that the inner volume is substantially sealed.

38. The apparatus of claim 21, wherein at least one of the sample bag, the sealing member, the imaging window, and the positioning member is reusable.

39. The apparatus of claim 38, wherein at least one of the sample bag, the sealing member, the imaging window, and the positioning member is configured to be sterilized in an autoclave before reuse.

40. The apparatus of claim 21, wherein the vacuum port can be sealed such that a partial vacuum can be maintained within the apparatus once the vacuum source is disconnected.

41. An apparatus for holding a biological tissue sample in a substantially fixed position, the apparatus comprising:
a sample bag defining an inner volume configured to receive the biological tissue sample;
a sealing member coupled to the sample bag;
an imaging window substantially spanning the opening of the sample bag and configured to be placed in contact with a portion of the biological tissue sample;
a positioning member coupled to the imaging window and configured to be disposed against the sealing member, the positioning member including a vacuum port disposed and configured to be aligned with a vacuum source to withdraw air from the inner volume of the sample bag; and
a locking mechanism including a channel, the channel having a first end that is substantially open and a second end that is substantially closed.

42. The apparatus of claim 41, further comprising:
an alignment element connected to the positioning member;
a first alignment marking indicating the first end of the channel; and
a second alignment marking indicating the second end of the channel,
wherein the alignment element is configured to move between the first alignment marking and the second alignment marking as the positioning member is rotationally connected to an imaging device; and
wherein alignment between the alignment element and the second alignment marking indicates proper alignment of the vacuum port with the vacuum system.

43. The apparatus of claim 41, further comprising:
a receiving member having a channel to which a portion of the positioning member is configured to be disposed; and
a plurality of registration points disposed about the receiving member and configured to arrest movement of the positioning member once a portion of the positioning member is disposed within the channel.

44. The apparatus of claim 41, wherein the positioning member includes a first portion and a second portion, the sealing member disposed between the first portion and the second portion such that the inner volume is substantially sealed.

45. An apparatus for holding a biological tissue sample in a substantially fixed position, the apparatus comprising:
a sample bag defining an opening and having an inner volume configured to receive the biological tissue sample;
a sealing member coupled to the opening of the sample bag;
an imaging window substantially spanning the opening of the sample bag and
configured to be placed in contact with at least a portion of the biological tissue sample;
a positioning member coupled to the imaging window and configured to be disposed against the sealing member, the positioning member including a vacuum port disposed and configured to be aligned with a vacuum source to withdraw air from the inner volume of the sample bag;
a receiving member having a channel to which a portion of the positioning member is configured to be disposed; and
a plurality of registration points disposed about the receiving member and configured to arrest movement of the positioning member once a portion of the positioning member is disposed within the channel.

46. The apparatus of claim 45, further comprising:
an alignment element connected to the positioning member;
a first alignment marking indicating the first end of the channel; and
a second alignment marking indicating the second end of the channel,
wherein the alignment element is configured to move between the first alignment marking and the second alignment marking as the positioning member is rotationally connected to an imaging device; and
wherein alignment between the alignment element and the second alignment marking indicates proper alignment of the vacuum port with the vacuum system.

47. The apparatus of claim 46, further comprising:
a locking mechanism configured to retain the portion of the positioning member disposed within the channel of the receiving member.

48. The apparatus of claim 47, wherein the locking mechanism includes a ridge configured to have a shape and a volume substantially similar to a shape and a volume of the channel.

49. The apparatus of claim 47, wherein the channel has a first end that is substantially open and a second end that is substantially closed.

50. The apparatus of claim 49, wherein further motion of the positioning member is disallowed once a distal end of the portion of the positioning member abuts the substantially closed second end of the channel.

51. The apparatus of claim 47, further comprising:
a plurality of registration points disposed about the receiving member and configured to arrest movement of the positioning member once a portion of the positioning member is disposed within the channel.

52. The apparatus of claim 47, wherein the receiving member is configured to be coupled to an imaging device such that the biological tissue sample is securely positioned against the sample window and readily available for analysis.

53. The apparatus of claim 45, wherein the inner volume is substantially sealed when the positioning member is disposed against the sealing member.

54. The apparatus of claim 45, further comprising:
a receiving member having a channel to which a portion of the positioning member is configured to be disposed, the channel defined at least in part by a first wall spaced a distance from a second wall.

* * * * *